(12) United States Patent
Ledoux et al.

(10) Patent No.: US 8,259,900 B1
(45) Date of Patent: Sep. 4, 2012

(54) ADAPTIVE SCANNING OF MATERIALS USING NUCLEAR RESONANCE FLUORESCENCE IMAGING

(75) Inventors: Robert J. Ledoux, Harvard, MA (US); William Bertozzi, Lexington, MA (US)

(73) Assignee: Passport Systems, Inc., Billerica, MA (US)

( * ) Notice: Subject to any disclaimer, the term of this patent is extended or adjusted under 35 U.S.C. 154(b) by 1773 days.

(21) Appl. No.: 11/511,182

(22) Filed: Aug. 28, 2006

Related U.S. Application Data

(63) Continuation of application No. 10/994,115, filed on Nov. 19, 2004, now Pat. No. 7,120,226.

(60) Provisional application No. 60/524,551, filed on Nov. 24, 2003.

(51) Int. Cl.
*G01N 23/04* (2006.01)
*G01N 23/223* (2006.01)
*G21K 1/10* (2006.01)
*H05G 1/60* (2006.01)
*G01B 15/00* (2006.01)

(52) U.S. Cl. ................ 378/57; 378/21; 378/23; 378/46; 378/90

(58) Field of Classification Search .......... 378/4–6, 378/21, 23–25, 46–49, 51, 57, 62, 70, 71, 378/76, 82, 86, 87, 90
See application file for complete search history.

(56) References Cited

U.S. PATENT DOCUMENTS

| | | |
|---|---|---|
| 3,496,357 A | 2/1970 | Putz et al. |
| 4,446,568 A | 5/1984 | Williams et al. |
| 4,788,704 A | 11/1988 | Donges et al. |
| 4,941,162 A | 7/1990 | Vartsky et al. |
| 5,115,459 A | 5/1992 | Bertozzi |
| 5,247,177 A | 9/1993 | Goldberg et al. |
| 5,323,004 A | 6/1994 | Ettinger et al. |
| 5,420,905 A | 5/1995 | Bertozzi |
| 5,600,303 A | 2/1997 | Husseiny et al. |
| 5,600,700 A | 2/1997 | Krug et al. |
| 5,642,393 A | 6/1997 | Krug et al. |
| 6,018,562 A | 1/2000 | Willson |
| 6,088,423 A | 7/2000 | Krug et al. |
| 6,108,396 A | 8/2000 | Bechwati et al. |

(Continued)

FOREIGN PATENT DOCUMENTS

JP 57-058625 A 4/1982
(Continued)

OTHER PUBLICATIONS

Office Action mailed Nov. 16, 2010 in Japanese Patent Application No. 2006-541575.
(Continued)

*Primary Examiner* — Anastasia Midkiff
(74) *Attorney, Agent, or Firm* — Foley Hoag LLP

(57) ABSTRACT

A method for detecting nuclear species in a sample by adaptive scanning using nuclear resonance fluorescence may comprise illuminating the target sample with photons from a source; detecting a signal in an energy channel; determining a scan evaluation parameter using the signal detected; determining whether the scan evaluation parameter meets a detection efficiency criterion; adjusting one or more system parameters such that the scan evaluation parameter meets the detection efficiency criterion; and comparing the signal in an energy channel to a predetermined species detection criterion to identify a species detection event. In another embodiment, detecting a signal in an energy channel may further comprise detecting photons scattered from the target sample. In another embodiment, detecting a signal in an energy channel may further comprise detecting photons transmitted through the target sample and scattered from at least one reference scatterer.

40 Claims, 5 Drawing Sheets

U.S. PATENT DOCUMENTS

| | | |
|---|---|---|
| 6,175,609 B1 | 1/2001 | Edic et al. |
| 6,345,113 B1 | 2/2002 | Crawford et al. |
| 6,442,233 B1 | 8/2002 | Grodzins et al. |
| 7,430,479 B1 | 9/2008 | Holslin et al. |
| 2004/0109532 A1 | 6/2004 | Ford et al. |
| 2005/0094765 A1 | 5/2005 | Biijani et al. |
| 2005/0111619 A1 | 5/2005 | Biijani et al. |

FOREIGN PATENT DOCUMENTS

| | | |
|---|---|---|
| JP | 05-100049 A | 4/1993 |
| JP | 3425600 T | 4/1997 |
| JP | 09-127021 A | 5/1997 |
| JP | 2002-243671 A | 8/2002 |
| WO | WO9939189 | 8/1999 |

OTHER PUBLICATIONS

Office Action mailed Jun. 28, 2011 in Japanese Patent Application No. 2006-541575.

Degener et al., Depole Excitations in $^{48}$Ti Studied by Nuclear Resonance Fluorescense, Nuclear Physic A513 (1990) 29-42.

Metzger, Electric Dipole Transitions from the 2.6 MeV septuplet in Bi209, Physical Review 187 (1969) 1680-1682.

International Search Report, Int'l App. No. PCT/US2004/039043.

Written Opinion of the International Searching Authority, Int'l App. No. PCT/US2004/039043.

Bertozzi, William, Poster: Material Identification and Object Imaging using Nuclear Resonance Fluorescense, Jul. 18, 2003, MIT, Dept. of Energy's Ofc of Nuclear Physics Workshop on the Role of the Nuclear Physics Research Community in Combating Terrorism.

ADAPTIVE SCANNING OF MATERIALS USING NUCLEAR RESONANCE FLUORESCENCE IMAGING

REFERENCE TO RELATED APPLICATIONS

This application is a continuation of U.S. application Ser. No. 10/994,115, filed Nov. 19, 2004, which is hereby incorporated herein by reference, and which claims the right of priority to U.S. Provisional Application No. 60/524,551, filed Nov. 24, 2003, which is hereby incorporated herein by reference.

BACKGROUND

This invention relates to nonintrusive scanning for materials (such as, for example, detection of explosives, nuclear materials, or contraband at airports, seaports, or other transportation terminals), and more particularly, to a method and apparatus for adaptive scanning using nuclear resonance fluorescence.

There are many requirements that scanning methods may desirably meet. First, it may be desirable that the measurements be reliable in detecting threats or contraband with a high probability of detection (DP) and a low probability of obtaining a false positive (FP). Further, it may be desirable that a scanning method operate as rapidly as possible while having a high rate of detection and a low rate of false positive events. Also, the searches may desirably be non-intrusive and non-destructive. Since the articles to be examined may be sizeable (such as shipping containers), the use of penetrating radiation is attractive; however, the radiation should preferably not leave the scanned article radioactive. The capability to image a target may also be of value. An adaptive method for optimally achieving these goals using Nuclear Resonance Fluorescence Imaging (NRFI) is presented here.

SUMMARY

Disclosed herein are methods and apparatus for detecting one or more nuclear species of interest in a target sample by adaptive scanning using nuclear resonance fluorescence. Also disclosed herein are methods and apparatus for adaptive non-invasive scanning of a target sample for detection of contraband, threats such as explosives or nuclear material, or other materials.

In one exemplary embodiment, a method for detecting a species in a target sample, may comprise illuminating the target sample with photons from a source; detecting a signal in at least one energy channel; determining a scan evaluation parameter using the signal detected in the at least one energy channel; determining whether the scan evaluation parameter meets a detection efficiency criterion; adjusting one or more system parameters such that the scan evaluation parameter meets the detection efficiency criterion; and comparing the signal in at least one energy channel to a predetermined species detection criterion to identify a species detection event. In another exemplary embodiment, determining the scan evaluation parameter using the detected signal may further comprise determining a background contribution to the signal in the at least one energy channel. In still another exemplary embodiment determining the scan evaluation parameter using the detected signal may further comprise determining the signal-to-noise ratio in the at least one energy channel. In still another exemplary embodiment, detecting a signal in at least one energy channel may further comprise detecting photons scattered from the at least a portion of the target sample in the at least one energy channel. In still another exemplary embodiment, detecting a signal in at least one energy channel may further comprise detecting photons transmitted through the target sample and scattered from at least one reference scatterer.

In another exemplary embodiment, a method for conducting a scan of a target sample for a potential threat may comprise providing a source of photons incident upon the target sample; measuring an energy spectrum of photons scattered from the target sample; computing at least one scan evaluation parameter using the energy spectrum of photons scattered from the target sample; determining whether a threat has been detected using the measured energy spectrum of photons scattered from the target sample. If a threat has been detected, the method may further comprise determining whether the at least one scan evaluation parameter meets a detection efficiency criterion. If the scan evaluation parameter does not meet the detection efficiency criterion, the method may further comprise adjusting one or more system parameters and repeating the steps of measuring the energy spectrum of scattered photons, computing a scan evaluation parameter, determining whether a threat has been detected, and determining whether the scan evaluation parameter meets the detection efficiency criterion. If the at least one scan evaluation parameter meets the detection efficiency criterion, the method may further comprise identifying a positive threat detection event.

In still another exemplary embodiment, the scan evaluation parameter may comprise a detection probability and the detection efficiency criterion may comprise the detection probability exceeding a minimum desired detection probability. In still another exemplary embodiment, the scan evaluation parameter may comprise a probability of obtaining a false positive result, and the detection efficiency criterion may comprise the probability of obtaining a false positive result being less than a maximum desired probability of obtaining a false positive result. In still another exemplary embodiment, the scan evaluation parameter may comprise a detection probability and a probability of obtaining a false positive result, and the detection efficiency criterion may comprise the detection probability exceeding a minimum desired detection probability and the probability of obtaining a false positive result being less than a maximum desired probability of obtaining a false positive result.

In another exemplary embodiment, a method for conducting a scan of a target sample for a potential threat may comprise providing a source of photons incident upon the target sample, such that at least some photons are transmitted through the sample; allowing at least some of the photons transmitted through the sample to scatter from at least one reference scatterer; measuring an energy spectrum of photons scattered from the at least one reference scatterer; computing at least one scan evaluation parameter using the energy spectrum of photons scattered from the at least one reference scatterer; determining whether a threat has been detected using the measured energy spectrum of photons scattered from the reference scatterer. If a threat has been detected, the method may further comprise determining whether the at least one scan evaluation parameter meets a detection efficiency criterion. If the at least one scan evaluation parameter does not meet the detection efficiency criterion, the method may further comprise adjusting one or more system parameters and repeating the steps of computing a scan evaluation parameter, determining whether a threat has been detected, and determining whether the scan evaluation parameter meets a detection efficiency criterion. If the at least one scan evaluation parameter meets the detection efficiency criterion, the method may further comprise identifying a positive threat detection event. In still another exemplary embodiment, the scan evaluation parameter may comprise a detection probability and the detection efficiency criterion may comprise the detection probability exceeding a minimum desired detection probability. In still another exemplary embodiment, the scan evaluation parameter may comprise a probability of obtaining a false positive result, and the detection efficiency criterion may comprise the probability of obtaining a false positive result being less than a maximum desired probability of obtaining a false positive result. In still another exemplary embodiment, the scan evaluation parameter may comprise a detection probability and a probability of obtaining a false positive result, and the detection efficiency criterion may comprise the detection probability exceeding a minimum desired detection probability and the probability of obtaining a false positive result being less than a maximum desired probability of obtaining a false positive result.

In another exemplary embodiment, a method for detecting a potential threat in a target sample may comprise providing a source of photons; illuminating the target sample with photons from the source; providing at least one photon detector to measure an intensity of photons scattered from at least a portion the target sample in at least one energy channel; determining a nominal background signal in each of the at least one energy channels of interest; computing a signal-to-noise ratio in each of the at least one energy channels of interest; adjusting one or more system parameters to improve the signal-to-noise ratio of the data collected in at least one of the at least one energy channels of interest; and identifying a threat detection event if the intensity of photons detected in at least one of the at least one energy channels of interest meets predetermined threat detection criteria. In further exemplary embodiments, the step of adjusting one or more system parameters may further comprise one or more of the following: altering an effective dwell time of the photons in a region of the target sample; inserting a filter into the source of photons, the filter comprising one or more nuclear species to absorb photons having selected energies or energy regions; where the photon source comprises a bremsstrahlung target struck by a beam of electrons, altering the energy of the electron beam; altering the intensity and/or collimation of the source of photons; altering the collimation of one or more photon detectors; inserting a filter in front of one or more photon detectors, the filter comprising one or more nuclear species to absorb photons having energies falling into selected energy regions; altering the angle at which one or more of the photon detectors views the target sample; and/or altering the spot area of the photon beam where it is incident on the target sample.

In another exemplary embodiment, a method for detecting a potential threat in a target sample may comprise providing a source of photons; illuminating the target sample with photons from the source; providing at least one photon detector to measure an intensity of photons scattered from at least a portion the target sample in at least one energy channel; providing a transmission detector for measuring an intensity of photons transmitted through the target sample as a function of a position on the target sample at which the photons illuminate the target sample; identifying at least one region of interest for further scanning using the intensity of photons transmitted through the target sample as a function of a position on the target sample at which the photons illuminate the target sample; determining a nominal background signal of photons scattered from at least one of the at least one regions of interest into each of the at least one energy channels of interest; computing a signal-to-noise ratio in each of the at least one energy channels of interest; adjusting one or more system parameters to improve the signal-to-noise ratio and/or the statistical precision in at least one of the at least one energy channels of interest; and identifying a threat detection event if the intensity of photons detected in at least one of the at least one energy channels of interest meets a predetermined threat detection criterion. In a further exemplary embodiment, the transmission detector may comprise an X-ray imager. In still further exemplary embodiments, the step of adjusting one or more system parameters may further comprise one or more of the following: altering an effective dwell time of the photons in a region of the target sample; inserting a filter into the source of photons, the filter comprising one or more nuclear species to absorb photons having selected energies or energy regions; where the photon source comprises a bremsstrahlung target struck by a beam of electrons, altering the energy of the electron beam; altering the intensity and/or collimation of the source of photons; altering the collimation of one or more photon detectors; inserting a filter in front of one or more photon detectors, the filter comprising one or more nuclear species to absorb photons having energies falling into selected energy regions; altering the angle at which one or more of the photon detectors views the target sample; and/or altering the spot area of the photon beam where it is incident on the target sample.

In another exemplary embodiment, a method for detecting a potential threat in a target sample may comprise providing a source of photons; illuminating the target sample with photons from the source; providing at least one reference scatterer, the reference scatterer comprising at least one nuclear species of interest; allowing photons transmitted through the target sample to scatter from the at least one reference scatterer; providing at least one photon detector to measure an intensity of photons scattered from the at least one reference scatterer in at least one energy channel; determining a nominal background signal in each of the at least one energy channels of interest; computing a signal-to-noise ratio in each of the at least one energy channels of interest; adjusting one or more system parameters to improve the signal-to-noise ratio in at least one of the at least one energy channels of interest; and identifying a threat detection event if the intensity of photons detected in at least one of the at least one energy channels of interest meets a predetermined threat detection criterion. In further exemplary embodiments, the step of adjusting one or more system parameters may further comprise one or more of the following: altering an effective dwell time of the photons in a region of the target sample; inserting a filter into the source of photons, the filter comprising one or more nuclear species to absorb photons having selected energies or energy regions; where the photon source comprises a bremsstrahlung target struck by a beam of electrons, altering the energy of the electron beam; altering the intensity and/or collimation of the source of photons; altering the collimation of one or more photon detectors; inserting a filter in front of one or more photon detectors, the filter comprising one or more nuclear species to absorb photons having energies falling into selected energy regions; altering the angle at which one or more of the photon detectors views the target sample; and/or altering the spot area of the photon beam where it is incident on the target sample.

In another exemplary embodiment, a method for detecting a potential threat in a target sample may comprise providing a source of photons; illuminating the target sample with photons from the source; providing a transmission detector for measuring an intensity of photons transmitted through the target sample as a function of a position on the target sample at which the photons, illuminate the target sample; identifying at least one region of interest for further scanning using the intensity of photons transmitted through the target sample as a function of a position on the target sample at which the photons illuminate the target sample; providing at least one reference scatterer, the reference scatterer comprising at least one nuclear species of interest; allowing photons transmitted through the at least one region of interest of the target sample to scatter from the at least one reference scatterer; providing at least one photon detector to measure an intensity of photons scattered from the at least one reference scatterer in at least one energy channel; determining a nominal background signal in each of the at least one energy channels of interest; computing a signal-to-noise ratio in each of the at least one energy channels of interest; adjusting one or more system parameters to improve the signal-to-noise ratio in at least one of the at least one energy channels of interest; and identifying a threat detection event if the intensity of photons detected in at least one of the at least one energy channels of interest meets a predetermined threat detection criterion. In a further exemplary embodiment, the transmission detector may comprise an X-ray imager. In still further exemplary embodiments, the step of adjusting one or more system parameters may further comprise one or more of the following: altering an effective dwell time of the photons in a region of the target sample; inserting a filter into the source of photons, the filter comprising one or more nuclear species to absorb photons having selected energies or energy regions; where the photon source comprises a bremsstrahlung target struck by a beam of electrons, altering the energy of the electron beam; altering the intensity and/or collimation of the source of photons; altering the collimation of one or more photon detectors; inserting a filter in front of one or more photon detectors, the filter comprising one or more nuclear species to absorb photons having energies falling into selected energy regions; altering the angle at which one or more of the photon detectors views the target sample; and/or altering the spot area of the photon beam where it is incident on the target sample.

In another exemplary embodiment, a method for detecting a potential threat in a target sample may comprise providing a source of photons; illuminating the target sample with photons from the source; providing at least one reference scatterer, the reference scatterer comprising at least one nuclear species of interest; allowing photons transmitted through the target sample to scatter from the at least one reference scatterer; providing at least one reference-photon detector to measure an intensity of photons scattered from the at least one reference scatterer in at least one reference-photon energy channel as a function of a position on the target sample at which the photons illuminate the target sample; using the intensity of photons measured by the reference-photon detector in each of the at least one reference-photon energy channels of interest to identify at least one region of interest for further scanning; providing at least one scattered-photon detector to measure an intensity of photons scattered from a region of interest in the target sample in at least one scattered-photon energy channel; determining a nominal background signal of photons measured by the at least one scattered-photon detector in each of the at least one scattered-photon energy channels of interest; computing a signal-to-noise ratio in each of the at least one scattered-photon energy channels of interest; adjusting one or more system parameters to improve the signal-to-noise ratio and/or the statistical precision in at least one of the at least one scattered-photon energy channels of interest; and identifying a threat detection event if the intensity of photons detected in at least one of the at least one scattered-photon energy channels of interest meets a predetermined threat detection criterion. In further exemplary embodiments, the step of adjusting one or more system parameters may further comprise one or more of the following: altering an effective dwell time of the photons in a region of the target sample; inserting a filter into the source of photons, the filter comprising one or more nuclear species to absorb photons having selected energies or energy regions; where the photon source comprises a bremsstrahlung target struck by a beam of electrons, altering the energy of the electron beam; altering the intensity and/or collimation of the source of photons; altering the collimation of one or more photon detectors; inserting a filter in front of one or more photon detectors, the filter comprising one or more nuclear species to absorb photons having energies falling into selected energy regions; altering the angle at which one or more of the photon detectors views the target sample; and/or altering the spot area of the photon beam where it is incident on the target sample.

In another exemplary embodiment, a method for conducting a scan of a target sample for a potential threat may comprise providing a source of photons incident upon the target sample such that some photons are scattered from the sample and some photons are transmitted through the sample; measuring an intensity of photons transmitted through at least a portion of the target sample; and using the measured intensity of photons transmitted through the at least a portion of the target sample to identify at least one region of interest for further study. In a further embodiment, the method may further comprise undertaking the following steps for at least one of the identified regions of interest: measuring an energy spectrum of photons scattered from the region of interest; using the energy spectrum of photons scattered from the region of interest to compute a detection probability and a probability of obtaining a false positive result; and using the measured energy spectrum of photons scattered from the region of interest to determine whether a threat has been detected. If a threat has not been detected, the method may further comprise determining whether the detection probability meets or exceeds a predetermined desired detection probability. If the detection probability meets or exceeds the predetermined desired detection probability, the method may further comprise ending the scan for the region of interest. If the detection probability does not meet or exceed the predetermined desired detection probability, the method may further comprise adjusting one or more system parameters and repeating the steps of measuring an energy spectrum of photons scattered from the region of interest; using the energy spectrum of photons scattered from the region of interest to compute a detection probability and a probability of obtaining a false positive result; and using the measured energy spectrum of photons scattered from the region of interest to determine whether a threat has been detected. If a threat has been detected, the method may further comprise determining whether the probability that the threat detection is a false positive signal exceeds a predetermined desired probability of obtaining a false positive result. If the probability that the threat detection is a false positive signal meets or exceeds the predetermined desired probability of obtaining a false positive result, the method may further comprise adjusting one or more system parameters and repeating the steps of measuring an energy spectrum of photons scattered from the region of interest; using the energy spectrum of photons scattered from the region of interest to compute a detection probability and a probability of obtaining a false positive result; and using the measured energy spectrum of photons scattered from the region of interest to determine whether a threat has been detected. If the probability that the threat detection is a false positive signal does not meet or exceed the predetermined desired probability of obtaining a false positive result, the method may further comprise identifying a positive threat detection event.

BRIEF DESCRIPTION OF THE DRAWINGS

These and other features and advantages of the method of adaptive scanning of materials using nuclear resonance fluorescence disclosed herein will be more fully understood by reference to the following detailed description, in conjunction with the attached drawings. The drawings illustrate principles of the apparatus disclosed herein, and are not to scale.

DETAILED DESCRIPTION OF EXEMPLARY EMBODIMENTS

To provide an overall understanding, certain illustrative embodiments will now be described; however, it will be understood by one of ordinary skill in the art that the devices and methods described herein can be adapted and modified to provide devices and methods for other suitable applications and that other additions and modifications can be made without departing from the scope of the systems described herein.

Unless otherwise specified, the illustrated embodiments can be understood as providing exemplary features of varying detail of certain embodiments, and therefore, unless otherwise specified, features, components, modules, and/or aspects of the illustrations can be otherwise combined, specified, interchanged, and/or rearranged without departing from the disclosed devices or methods. Additionally, the shapes and sizes of components are also exemplary, and unless otherwise specified, can be altered without affecting the disclosed devices or methods.

A beam of photons having a continuous energy spectrum incident on a target can excite nuclear resonances or states in the target which subsequently fluoresce. The resulting emission spectra are uniquely tied to the specific isotopes contained in the target. When detected by systems of detectors or detector arrays capable of resolving spatial information, these spectra allow for a measurement of the spatial distribution of isotopes contained in the irradiated volume.

Some exemplary systems for employing resonant scattering measurements (also called nuclear resonance fluorescence or NRF) in nonintrusive scanning applications are discussed in U.S. Pat. No. 5,115,459, Explosives Detection Using Resonance Fluorescence of Bremsstrahlung Radiation, and U.S. Pat. No. 5,420,905, Detection of Explosives and Other Materials Using Resonance Fluorescence, Resonance Absorption, and Other Electromagnetic Processes with Bremsstrahlung Radiation, the contents of both of which are hereby incorporated by reference.

Figure 1:
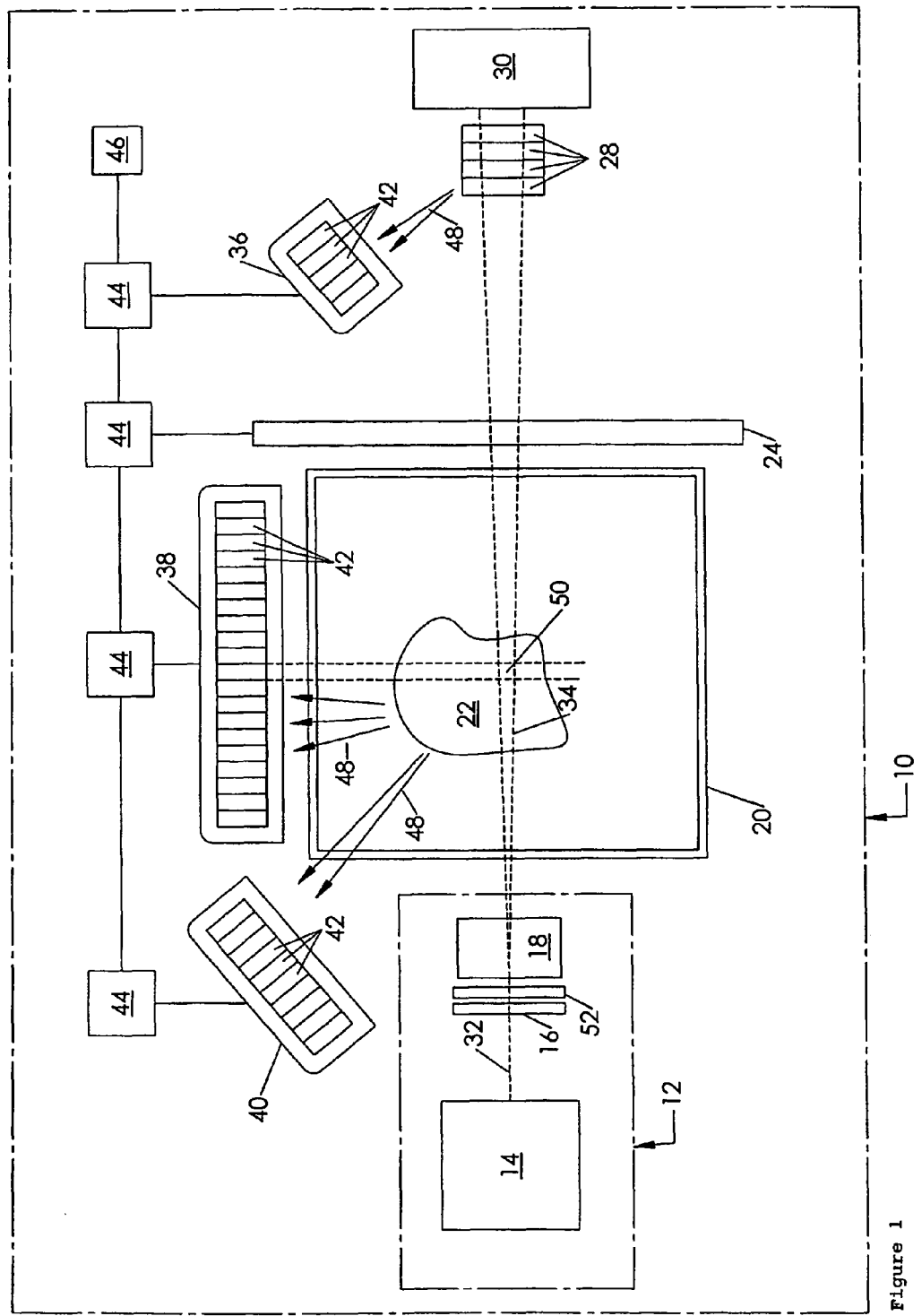
FIG. 1 is a schematic illustration of an embodiment of a system that may be used for adaptive scanning of materials using nuclear resonance fluorescence.

A schematic diagram of an exemplary embodiment of a nuclear resonance fluorescence imaging (NRFI) scanner configuration is shown in FIG. 1.

The system includes a photon source 12 producing photons having an energy spectrum over some energy range. Suitable photon sources include: a bremsstrahlung source; a Compton-broadened photon source using nuclear decay from a radioactive source; coherent bremsstrahlung radiation; free electron lasers; laser backscatter from high energy electrons; or other photon sources known to those skilled in the field.

In the illustrated embodiment, the photon source 12 is a bremsstrahlung source and may include an electron source 14 providing a beam of electrons 32 incident on a bremsstrahlung target 16 to generate a bremsstrahlung photon beam 34. The bremsstrahlung target 16 may be followed by a beam stopper (not illustrated) to stop the electrons 32. A filter 52 may follow the beam stopper, for example to filter out low energy photons from the bremsstrahlung beam 34, or to preferentially absorb photons in energy regions corresponding to particular NRF lines. A collimator 18 may be employed to collimate the bremsstrahlung beam 32. Shielding (not illustrated) may enclose the photon source 12. A description of an exemplary suitable bremsstrahlung photon source may be found in U.S. Pat. No. 5,115,459.

A target 20 to be scanned, such as a cargo container, shipping container, luggage, package, or other container or object, may be placed in the path of the bremsstrahlung beam 34. In one embodiment, the target may be moved through the path of the beam, for example by a conveyor belt. In another embodiment, the beam 34 may be scanned across the target 20, for example, by moving photon source 12 or steering the electron beam 32. The target 20 may contain target contents 22. Other ways of achieving scanning of the photon beam 34 over the target container 20 will be rocognized by those skilled in the art. The incident photon beam 34 resonantly excites the nuclei of the target's contents 22, and photons 48 may be both scattered from the contents 22 and the target 20 as well as transmitted through the contents 22 and the target 20. The energies of the scattered photons are characteristic of the spacings between the quantized energy states of the nuclei of the target contents 22 and the target 20. Each isotope present in the target contents 22 resonantly scatters photons in a unique set of energies.

Detecting apparatuses 38 and 40, which may include an array of detectors 42, may capture, measure, count, and/or record the energies of the photons scattered in a given direction or directions. A description of several exemplary suitable detecting apparatuses may be found in U.S. Pat. No. 5,115,459. The detecting apparatus 38 or 40 may further include a filter over the face of each detector to absorb low energy photons, and shielding (not illustrated). As scattering from the collimating aperture 18 could lead to a significant amount of photons directed toward the detecting apparatus 38 or 40, a shadow shield (not illustrated) between the collimator and the detecting apparatus 38 or 40 may be employed. A beam dump 30 may be provided to absorb the energy of the beam 34 that is not absorbed as the beam 34 passes through the target 20. Shielding (not shown) may enclose the entire device while allowing convenient means for the entry and exit of targets. Data from the detecting apparatus 38 or 40 is sent to a processor 46 which may analyze the data. The processor 46 may comprise a PC, microcomputer, or other suitable processor. One analysis may include determining the abundances of particular nuclear species of interest. The data may be preprocessed by preprocessing electronics 44, which may include preamplifiers filters, timing electronics, or other appropriate preprocessing electronics. The processor 46 may be adapted to evaluate the data to determine whether the contents of the target volume meet or exceed one or more predetermined detection thresholds. For example, the processor 46 may compare the data for each irradiated target volume to profiles of "normal" target volumes to determine whether the irradiated target volume should be considered "suspicious." In addition, the processor 46 may be programmed with other threat detection heuristics as described below. Further, as described in more detail below, the processor 46 may control a variety of parameters of the photon beam, scanning, detection, and/or other aspects of the system.

In order to minimize the effects of Compton scattering and other scattering processes and maximize the signal-to-noise ratio, the detecting apparatus 38 or 40 may be placed at an angle with respect to the bremsstrahlung beam 34 of more than 90 degrees relative to the direction of the photon beam, preferably substantially more than 90 degrees.

The beam 34 passes through the target contents 22. This beam may be absorbed in a beam dump 30 designed to absorb substantially all of the remaining energy. For example, a suitable beam dump for 10 MeV may include a layer of a hydrogenous material containing boron or lithium, a layer of carbon, and a layer of iron in a very deep cavity formed in a shield of lead and/or iron to shield the sides and the detectors from back-streaming low energy photons. A layer of a hydrogenous material containing boron or lithium may surround the outside of this shield. The depth of this cavity, the beam dimensions, the directive collimation of the detectors, and the exact location of the detectors are related parameters that may be made compatible so as to minimize the number of backward-streaming photons from the beam dump entering the detectors. Additional shadow shields may be set up to help meet this goal.

Imaging can be achieved in a variety of ways with the technique of the present invention. The luggage can be scanned with the beam by moving the entire photon source 12, the target 20, or simply the aperture 18. The electron beam may also be deflected by a magnet to sweep the bremsstrahlung beam direction. Preferred photon beam geometries include spots (cones) and stripes. Other suitable scanning configurations, geometrics, and patterns may be recognized by those skilled in the art and may be employed.

For example, if the beam 34 is collimated using a small circular aperture 18 to an average angle of approximately 1/20 radians (about 3 degrees), the spot 1 meter from the aperture will be about 10 cm across, a suitable size for imaging the contents of a piece of luggage or the contents 22 of a container 20.

If the photon beam 34 is collimated using a vertical slit aperture to produce a thin stripe of 10 cm width at the point of incidence with a piece of luggage, for example, a 60 cm long suitcase could be scanned in a few seconds as the suitcase moves on a conveyor belt. Alternatively, the beam 34 could be collimated into a spot swept vertically by an adjustable collimator or by magnetic deflection of the electron beam 32 used to generate the photon beam 34. Even if the collimation is in the form of a vertical stripe, the central intensity remains the highest, reflecting the natural collimation, and magnetic deflection of the electron beam 32 may be useful for imaging. If the collimation is a vertical stripe or a stripe of another orientation, the intersections of the stripe with the collimated views of the detectors 42 define voxels that are also useful for imaging.

In another technique, a large portion of the target container 20 may be flooded with bremsstrahlung radiation by using a large aperture, and the detectors 42 may be adapted to be direction-specific by, for example, introducing a collimator in front of each detector 42. In this way, each detector can be designed to only detect photons scattered from a small specific region 50 of the target contents 22 in a particular direction. Each such specific region or "voxel" 50 may be conceptualized as the three dimensional intersection of the photon beam 34 with the line of sight of a collimated detector 42. An array of such detectors can be designed to image the entire target 20 to a desired degree of resolution.

Alternative detection systems adapted for obtaining spatially resolved images of target contents will be recognized by persons of skill in the art. Such detection systems may include, for example, detector arrays equipped with coded aperture systems that enable two-dimensional or three-dimensional spatial information to be resolved. Imaging techniques such as those employed in processor 46 tomography (CT) may also be employed to obtain two- or three-dimensional images of the target 20 and its contents 22.

A combination of the above imaging techniques results in a further embodiment of the present invention. For example, a thin slit aperture could be used to irradiate thin vertical strips of the target 20 as the target 20 moves on a conveyor belt. The width of the strip will determine the horizontal resolution of the imaging. The vertical resolution could be increased by using directional detectors aimed at intervals along the vertical height of the illuminated area. Such a method would result in fast measurements at a high resolution.

Use of a rapidly adjustable photon beam collimating aperture 18 results in further embodiments with important advantages. For example, a target 20 could first be flooded with bremsstrahlung radiation in an effort to detect explosives in the form of thin sheets and/or to obtain an initial estimate of the abundances of various elements in its contents. The collimating aperture 18 could then be stopped down to image the suitcase in an effort to detect more localized explosive materials. In one embodiment, the processor 46 may control the size of the collimating aperture 18 in response to any positive signal detected in an initial low-resolution scan, as will be discussed further below.

The processor 46 may be adapted to analyze the data obtained by the detecting apparatus in any combination of 38 and/or 40. As with other explosives detecting devices, profiles of elements, such as nitrogen and oxygen, as they appear in "normal" target volumes or voxels may either be modeled or experimentally determined. A target volume or voxel 50 or a combination of volumes or voxels 50 which deviates significantly from these profiles may be identified as "suspicious." The processor 46 can be adapted to compare data to stored profiles. If the profiles are rigorously determined, a high probability of explosives detection ("detection probability" or "DP") accompanied by a low rate of false alarms ("false positives" or "FP") may be achieved. If a region of a target shows the explicit elemental profile of an explosive the threat identification may be determined.

The detection methods thus described, in which resonant scattering from the target 20 and target contents 22 is detected by detectors 40, may be employed to obtain three-dimensional NRF imaging of the target contents 22. For example, if each detector 40 is adapted to be directional (as by collimation, for example), then the NRF spectrum detected in each detector provides a measure of the isotopes contained in each voxel 50 where the field of view of each detector 40 intersects the photon beam 34. These spectra may, if desired, be reconstructed as a 3-D isotopic image of the target contents 22. For that reason, the detection methods described above may be referred to as 3-D NRF imaging.

To extract information about the abundance of each species identified in the NRF spectrum, it is necessary for the system to first obtain an approximation of the photon flux incident upon each voxel 50. In one embodiment this may be achieved by observing the scattered photon spectra from each voxel 50 along the path of the photon beam 34 and, using the observed spectra to compute an average attenuation of the beam 34 in each voxel 50, and adjusting the estimated incident flux on each successive voxel 50 based upon the attenuation in each of the previous voxels. Thus, in an exemplary embodiment, the incident flux on the first voxel 50 where the beam 34 initially strikes the target 20 is known. The spectrum of photons scattered from the first voxel may then be fit. In one embodiment, the fit may be a complete model that includes contributions such as the resonant scattering peaks plus background due to Compton scattering, pair production, and photoelectric effects in the detector and nonresonant background contributions. The isotopic composition of the first voxel may be extracted from the result of that fit, using such information as the known incident flux on the first voxel, the known interaction cross sections for the observed NRF resonances, the known detector efficiencies, etc. From the measured spectrum and/or from the measured isotopic composition of the first voxel, the attenuation of the photon beam 34 as it passes through that first voxel may be determined and used to compute an estimate of the incident flux on the second voxel. The fitting process may then be repeated for the second voxel, and the incident flux for the next subsequent voxel determined from the attenuation the second voxel, and so on along the path of the photon beam 34 through the target 20. In some embodiments, the incident photon flux on each voxel along the beam may be determined as a function of energy using known absorption characteristics and measured abundances of the isotopes identified in the previous voxels along the photon beam 34. As will be discussed further below, these computed incident photon fluxes may be used in computing a minimum number of photons scattered in a particular energy channel from a particular voxel that will be considered a threat. This procedure may be iterated and further constrained by, for example, measuring the total transmitted flux and incorporating that information into the fit to the complete energy spectrum from each voxel 50.

An alternate detecting scheme is also illustrated in FIG. 1. This alternate scheme can provide a 2-D NRF image of the isotopic composition of the target contents 22. As the photon beam 34 passes through the target 20, photons will be resonantly absorbed by the nuclei of the target contents 22. The energies of the absorbed photons correspond to the spacings between the quantized energy states of each nuclear species in the target 20. For these specific energies, the transmitted beam will be depleted of photons. For example, if the target contains nitrogen, photons of energies corresponding to the spacings between nuclear energy states in nitrogen will be selectively absorbed. The amount of photons absorbed depends on the quantity of nitrogen in the target 20. Thus, the intensities of the photons of specific energies transmitted through the target contain information about the nuclear composition of the target. A series of reference resonance scatterers 28 may be arranged behind the target 20. Each reference scatterer 28 may be composed of one or more of the elements that the explosives detecting device is to detect. An array 36 of detecting apparatuses 42 may be adapted to capture, measure, count, and record the photons 48 resonantly scattered from each of the reference scatterers 28. For example, in a simple embodiment, two reference scatterers are provided, one of nitrogen, the other of oxygen. In such an embodiment, a detecting apparatus may be adapted to detect photons resonantly scattered from the nuclei in the nitrogen scatterer and another detecting apparatus may be adapted to detect photons resonantly scattered from the nuclei in the oxygen scatterer. Alternatively, a single detecting apparatus 42 may be adapted to detect photons resonantly scattered from nuclei in all the reference scatterers 28.

This detecting scheme operates as follows. If no target 20 is placed in the path of the beam 34, the photon beam will directly strike the first of the reference resonance scatterers 28. The detecting apparatus 36 associated with the first reference scatterer will detect a relatively large amount of photons corresponding to a nuclear species contained in the first reference scatterer, because there will have been essentially no absorption at energies corresponding to such a species. Likewise, if a target 20 containing only a relatively small amount of a nuclear species contained in the first reference scatterer is placed in the path of the beam, this strong signal at the first detecting apparatus will be diminished by only a relatively small amount. If however, a target 20 with a relatively large amount of the nuclear species contained in the first reference scatterer is placed in the path of the beam, this signal will be diminished considerably, due to the resonant absorption in the target 20 of the photons of energies corresponding to that nuclear species.

Thus, an abundance of a nuclear species of interest in a target 20 and its contents 22 will be detected as a decrease in the signal from the detecting apparatus associated with a reference scatterer containing that nuclear species. Photons of energies not corresponding to the nuclear species of which a reference scatterer is substantially composed will be attenuated due to non-resonant processes by only a relatively small amount. Thus, the method of detecting the nuclear species of the first reference scatterer extends to each subsequent reference scatterer. An advantage of this detecting scheme is that if the energies corresponding to two or more nuclear species of interest are very close, the detecting apparatus 38 or 40, detecting directly scattered photons, may have difficulty distinguishing the contributions from the two or more nuclear species. However, using the transmitted photons and reference scatterer 28, the energies corresponding to each nuclear species are detected separately, this ambiguity is diminished considerably, and the ability of the detecting apparatus to resolve closely spaced photon energies is no longer very important. When the energies corresponding to two or more nuclear species do not interfere, a single reference scatterer can be composed of a combination of the species.

It is a further advantage of this detection scheme that it may allow the total amount of material of a nuclear species corresponding to a nuclear species contained in a reference target to be measured quickly and with a relatively small number of detectors. This may allow, for example, a rapid first-pass scan of the target 20 for the presence of any amount of one or more nuclear species of interest, before a more detailed scan or imaging procedure is undertaken. Where such a rapid first-pass scan shows that no threatening quantities of nuclear species of interest are present, more detailed scans may be bypassed, for a savings of time and resources.

In the embodiment illustrated in FIG. 1, the system may also include a direct transmission detector 24, such as an X-ray imager, which can measure the intensity and/or energy of photons transmitted through the target 20 as a function of the lateral position in which the photon beam strikes the target. Such a measurement could be used, for example, to obtain a map of the average density of the target 20, projected along the axis of the photon beam 34. In this way, a very precise image of the transmission density of the target can be constructed. Such an image will identify specific areas of high material density in the target which would be a further aid in detecting explosive or high atomic number materials. (Similar density imaging could also be achieved by detecting the back-scatter from the target 20, especially at low energies).

A direct transmission detector 24 or the 2-D NRF detection scheme described above in which photons transmitted through the target 20 are allowed to scatter from reference scatterers 28 may also provide an estimate of the total attenuation of the photon beam 34 as it passes through the target 20. In some embodiments, the total attenuation of the photon beam 34 may be used as a check of (or to provide a means for iteratively correcting) the determination described above of the photon flux entering each voxel along the beam, as noted previously.

Using NRF to Identify the Presence of Nuclear Species of Interest

Figure 2:
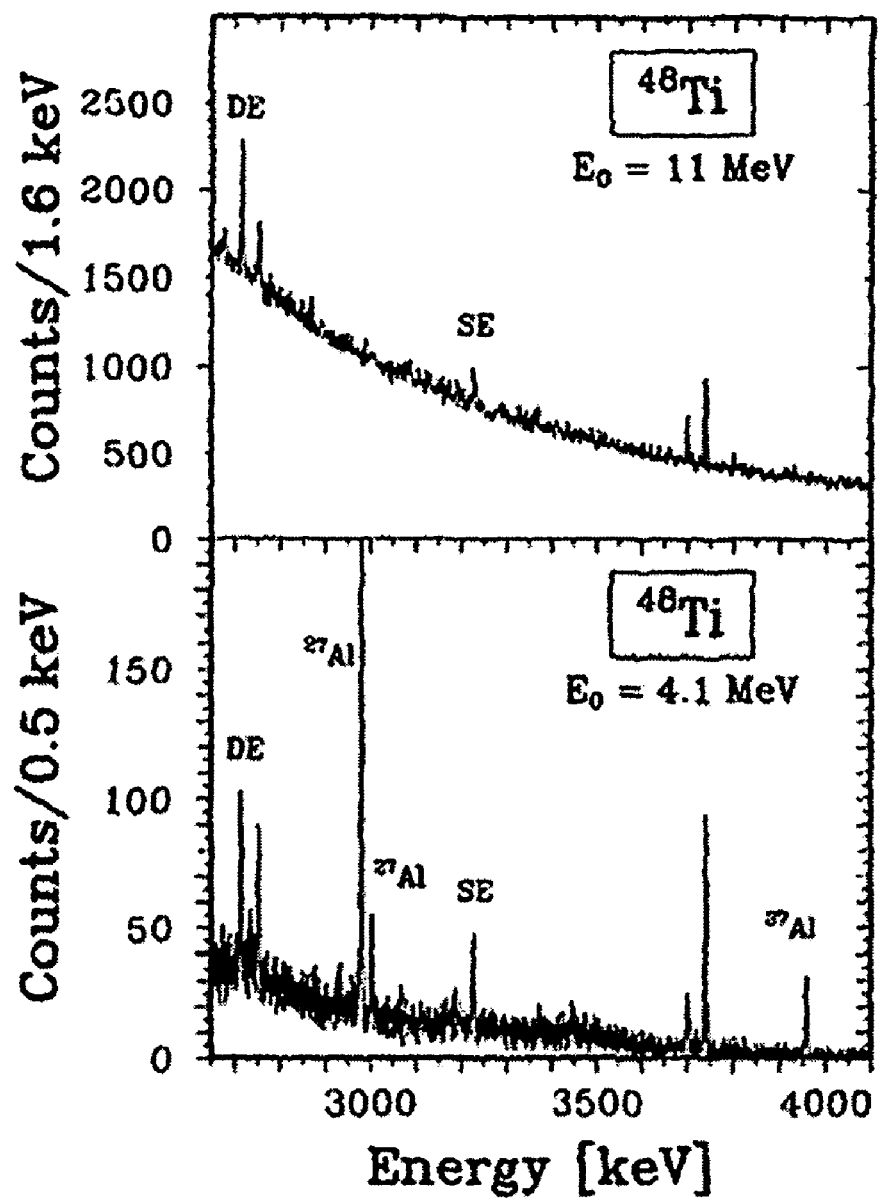
FIG. 2 illustrates NRF spectra of $^{48}$Ti and $^{27}$Al made with bremsstrahlung photon beams generated with electron beams at 4.1 MeV and 11 MeV.

The usefulness of Nuclear Resonance Fluorescence to identify nuclear species present in a target or to detect species of interest is illustrated in FIG. 2. Nuclear Resonance Fluorescence spectra for the isotopes $^{48}$Ti and $^{27}$Al (present in the 4.1 MeV spectrum only) obtained from a bremsstrahlung beam produced by electron beams with 4.1 and 11 MeV end-point energies are displayed in FIG. 2. (These spectra are described in Degener, et al, Nuclear Physics A513 (1990) 29-42, the contents of which are hereby incorporated by reference.) The spectra were measured using a collimated high energy resolution germanium detector at angles greater than 90 degrees with respect to the beam direction. The narrow peaks (having a width of approximately 4 keV, limited by detector resolution) of the measured NRF states for $^{48}$Ti and $^{27}$Al are easily detected against the continuous and slowly varying non-resonant background. The continuous background resulting from non-resonant background processes is observably higher for the higher end-point energy when looking at states of a fixed energy.

Figure 3:
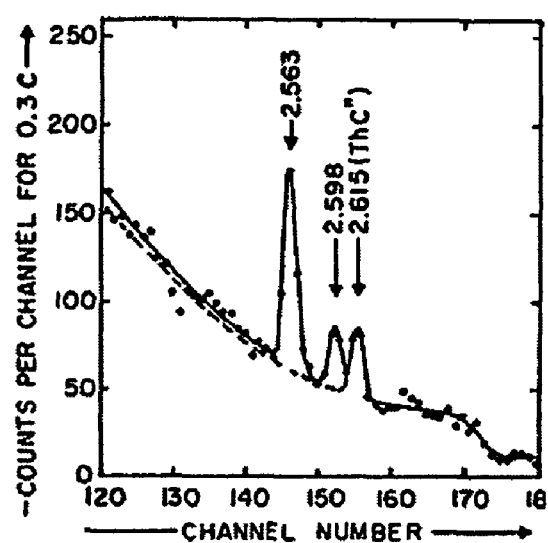
FIG. 3 illustrates NRF spectra of $^{209}$Bi and $^{208}$Pb made with bremsstrahlung photon beams generated with electron beams at 2.72 MeV.

The characteristics of the energy spectra from non-resonant processes such as Compton scattering and pair production, also directly provide information on the density and average atomic number (Z) of the volume under inspection. This is illustrated in FIG. 3, in which the NRF spectrum for a $^{209}$Bi target are superimposed with that of $^{208}$Pb under identical experimental conditions. (These spectra are described in F. R. Metzger, Physical Review 187, pg. 1680 (1969), the contents of which are hereby incorporated by reference.) The $^{209}$Bi spectrum (solid curve) shows the presence of two strong NRF states (the third peak is from a contaminant in the target) while the $^{208}$Pb spectrum (dashed curve) has a smooth continuous background since this isotope does not have any NRF states in this energy region. The Z of $^{208}$Pb and $^{209}$Bi are 82 and 83, respectively, and as expected from theory and borne out in these measurements, the non-resonant background processes are essentially identical.

These spectra and the similar spectra obtained in other known NRF experiments illustrate a number of points:

The use of high energy-resolution detectors allows the straightforward extraction of the intensity of NRF states in the presence of a non-resonant background and hence the quantity of material in the region being probed associated with each isotope for which an NRF state is excited.

The non-resonant background is dependent on the atomic number (Z), density and amount of the target sample, in a way which can be measured or modeled.

The non-resonant background underlying an NRF state is a function of the bremsstrahlung beam end-point energy, and the Z of the target material.

The method proposed here may also incorporate a two-dimensional transmission detector 24 such as an X-ray imager that may sample the integrated attenuation with relatively high spatial resolution. This complementary detector enables the detection of small dense objects. It can be used in connection with the NRF 3-D image and/or the NRF 2-D transmission detector to dynamically identify regions of interest for further scanning as part of the adaptive system or for other purposes.

The signal to noise ratio for the measurement of a given NRF state relative to the non-resonant background may be determined by the phenomenon described above. The properties of the NRF states, including the scattering cross sections as a function of energy and angle for each nuclear species of interest, may be known prior to scanning. The number of photons scattered from a target voxel 50 and detected at a particular scattering angle at the characteristic energy or energies of the NRF state(s) associated with a particular nuclear species of interest are proportional to the abundance of that species in the target voxel. Measurements of the number of counts in an energy channel corresponding to a given NRF state and an estimate of the contribution of background non-resonant processes to the counts in that energy channel (such as the average background counts due to non-resonant processes in neighboring energy intervals, or other estimates of the expected background) can be used to estimate adaptively the detection probability (DP) and the probability of obtaining a false positive result (FP) for a given quantity of a specified isotope in the region of space being examined. This information can be used to modify the parameters of the scan so as to satisfy desired criteria for DP and FP. In some embodiments, measurement of the number of counts in an energy channel of interest together with an estimate of the contribution of the non-resonant background to that number of counts can provide a dynamic evaluation of the signal-to-noise ratio which can be used to adaptively modify scan parameters to satisfy desired DP and FP criteria. For example, if the region under examination has a relatively high non-resonant background, the signal-to-noise ratio will be lower and the dwell time of the bremsstrahlung beam can be increased to compensate by collecting more photon events in order to achieve higher statistical accuracy, or other system parameters may be adjusted to improve signal-to-noise or statistical accuracy as discussed in more detail below.

Although the following discussion of an exemplary method of adaptive scanning uses a dynamic determination of the signal-to-noise ratio to determine whether desired DP and FP criteria are achieved, it will be understood by those skilled in the art that the measurement of the number of counts in the energy channel or channels of interest and the measured, estimated, or approximated background, particularly as a function of energy, may be considered independently in determining DP and FP. For example, in cases where there is no appreciable background in an energy channel or energy region of interest, all counts in that channel or region may be attributable to the presence of an isotope corresponding to that channel or region, and a determination of whether a threshold quantity of that isotope exists may be made without the step of determining the signal-to-noise ratio.)

Example of the Adaptive Scanning Method

An exemplary embodiment of a method of adaptive scanning of a target to identify threshold quantities of nuclear species of interest will now be described. In the embodiment described, threshold quantities of nuclear species of interest may be described as "threats," and an aim of the method may be adaptive scanning of cargo containers, luggage, or other targets to detect the presence of threats such as nuclear material or conventional explosives. However, it will be understood by persons of skill in the art that the methods disclosed herein may be applied to any application in which nonintrusive scanning of a target to identify the isotopic composition of the target or to detect threshold quantities of particular species of interest is desired. Such applications may include (without limitation) scanning cargo containers to determine whether their contents match the associated shipping manifests, and/or identifying the presence of toxic substances such as Sarin, Phosgene, or other agents, in addition to scanning targets for the presence of nuclear materials, quantities of high-density materials (which may indicate shielded nuclear or other materials), explosives, or contraband.

In one embodiment, an initial flux of photons may be injected into a voxel 50 in the target 20, and the spectrum of photons detected at the corresponding detector 42 may be analyzed by fitting to a curve that accounts for the non-resonant background and the contributions from any resonance peaks that may be present. The processor 46 may also collect the number of counts in an energy channel or energy channels of interest that correspond to energy level spacings in nuclear species of interest.

The processor 46 may use this initial observation to make a first approximation of the background in each energy channel of interest. In one embodiment, a first approximation to the background (i.e., non-resonant) contribution to the signal detected in an energy channel corresponding to a nuclear resonance transition in a species of interest may be obtained by averaging the number of counts detected in the adjacent channels if they do not occur at the energy of an NRF line. The background may also be estimated by, for example, a 1/E distribution, in particular a 1/E distribution fit locally to the energy region of interest. Corrections to the estimated background may be applied. For example, for every resonant photopeak detected in a detector, there will also be known, non-resonant, lower energy scattered photons associated with that resonant signal. Thus, the estimated background may be corrected by subtracting any resonant and non-resonant signal detected that is known or recognized to correspond to any particular nuclear species. The estimated background may take into account the attenuation of the photon beam as it passes through and interacts with the target contents 22 on its way to the voxel 50 under observation. In one embodiment, this attenuation may be measured by direct scattering measurements in detectors arrays 38 or 40, or by estimates of the average density of the target 20 obtained from weighing the target 20, referring to a cargo manifest, or measuring the intensity of transmitted photons using apparatus such as x-ray imager 24 or transmission detectors 36 with reference scatterers 28.

The processor 46 may use the estimated background together with other parameters to generate a threshold threat signal for each nuclear species of interest. Such a threshold threat signal could be a number of counts or a number of counts over background in a particular channel. The threshold threat signal may be generated, for example, by consulting preprogrammed tables identifying threshold signal amounts for various species at various amounts of incident photon flux. (The incident photon flux as a function of energy may be determined for each voxel 50 along the photon beam 34 as described previously.) For example, in one embodiment, a processor 46 may be programmed in advance with the a table of or means for computing an expected number of counts detected as a function of energy in regions of the target having particular species of interest present in particular amounts, for a given input photon flux and/or a given background. For example, the processor 46 may be programmed with the number of counts corresponding to the presence of typical threat levels of selected species of interest for a given input photon flux and/or a given background. In one embodiment, this number of counts may be the number of photons scattered into a particular energy channel or channels from a voxel 50 in the target 20 (corrected for the measured or estimated attenuation of the photon beam as it penetrates the target), measured at detector array 38 or 40. Alternatively, this number of counts may be the number of photons transmitted through the target 20 and scattered off of one or more reference scatterers 28 into a particular energy channel or channels measured in detector array 36.

Based upon one or more of the factors that contribute to the first estimation of the background, the processor 46 may establish an initial nominal set of photon beam parameters that are estimated to provide a particular level of background in an energy channel or energy channels of interest. For example, the processor 46 may determine an initial dwell time that, given the estimated background, is expected to provide a statistically significant measurement in an energy channel for which the threat detection threshold is a small signal.

The processor 46 may then make a measurement in one voxel 50 (or set of voxels along the present position of the photon beam 34) at that initial dwell time, and dictate the system response based upon the result of that measurement. For example, if the detected signal is not larger than the threat detection threshold corresponding to the estimated expected background signal in any energy channel of interest, the processor 46 may proceed to the next voxel. On the other hand, if the detected signal exceeds the threat detection threshold in some energy channel of interest, the processor 46 may compute a dynamic measurement of the signal-to-noise ratio in that channel (by, e.g, comparing the detected signal with the expected background signal or measured background signal). The processor 46 may use this information to determine whether the signal represents a statistically significant threat detection event as follows.

Figure 4A:
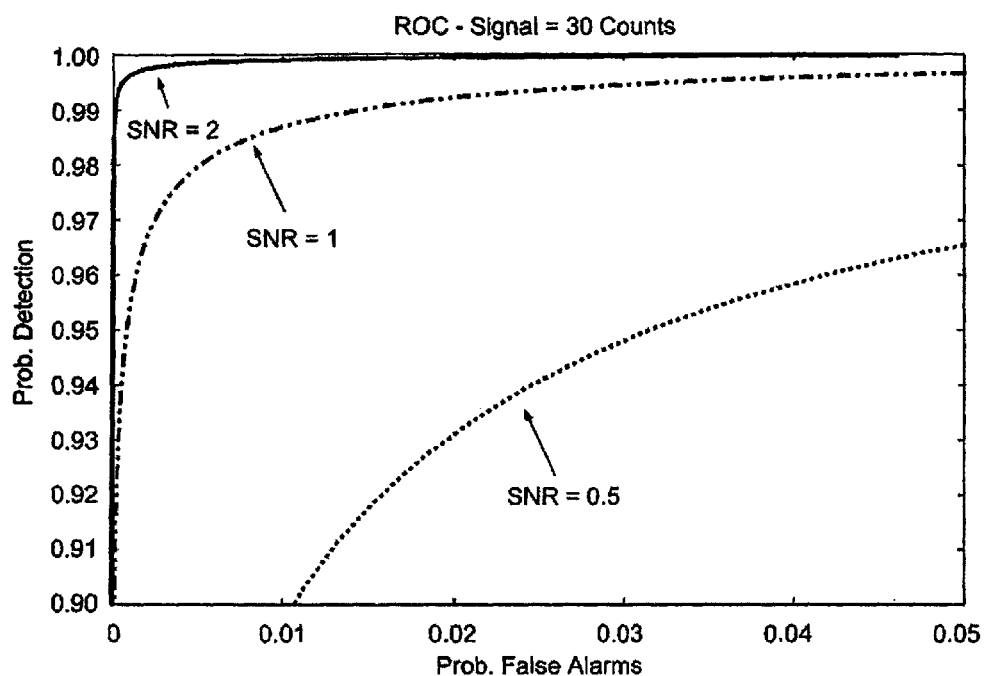
FIG. 4 illustrates typical Receiver Operator Characteristic (ROC) curves for three signal-to-noise ratios, calculated for a signal of 30 counts (FIG. 4a) and a signal of 42 counts (FIG. 4b)
Figure 4B:
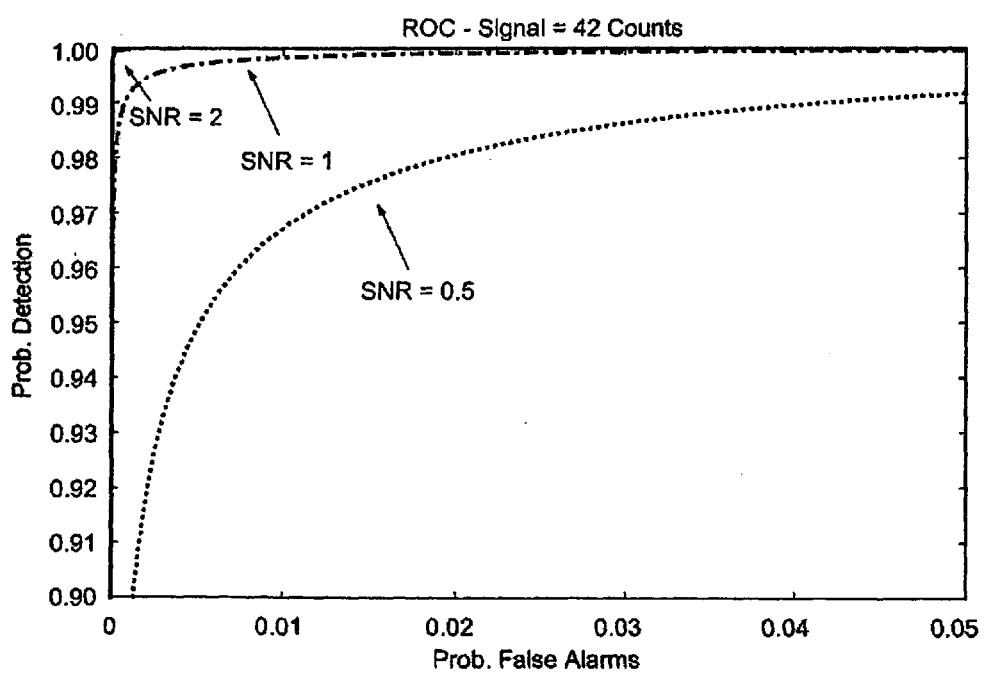

In one embodiment, the processor 46 may refer to a Receiver Operator Characteristic (ROC) curve in evaluating the significance of an initial threat detection event. An exemplary set of ROC curves is illustrated in FIG. 4a and FIG. 4b, at two different average numbers of counts (30 and 42) detected as signal from a given threat mass, with curves for three values of signal-to-noise shown for each average count number: 2, 1 and 0.5. These exemplary curves were computed using statistical considerations along with the assumed signal-to-noise ratio corresponding to each curve. In the general case, a computation of detection probability (DP) versus the probability of obtaining a false positive result (FP) could incorporate systematic errors and other non-statistical uncertainties. The curves illustrated in FIG. 4a and FIG. 4b represent the relationship between DP and FP for threat detections for a nominal beam parameters that would yield 30 counts or 42 counts, respectively, for a NRF state at a given minimal threat mass in the examination volume. Each point on each ROC curve represents the relationship between DP and FP for a given threshold. The curves therefore reflect that for fixed signal-to-noise, if the probability of detection is increased by lowering the detection threshold, the corresponding likelihood of a false positive must increase.

With reference to FIG. 4a, where the nominal beam parameters for a given threat mass would yield 30 signal counts, if the desired detection probability (DP) is greater than 98% with less than 2% false positive (FP) threat detection—that is, if the system is desired to identify at least 98% of voxels containing more than the minimal detection quantity of the particular species with at most 2% of identified voxels being falsely identified as containing more than that quantity—this criterion may be satisfied within the nominal beam parameters if the adaptive measurement of the signal-to-noise ratio is 1 or 2, but not if it is 0.5. As can be seen with reference to FIG. 4b, a criterion of greater than 98% DP with no more than 2% FP could be satisfied at a signal-to-noise ratio of 0.5 if 42 counts were accumulated instead of 30. (The threat threshold associated with the point where curve for the 0.5 signal-to-noise ratio crosses 98% DP and 2% FP corresponds to a threat detection threshold of 103 integral counts (signal and background). Thus, once the signal-to-noise is determined to be 0.5, the desired DP ($\geq$98%) and FP ($\leq$2%) may be achieved by adaptively adjusting scan parameters to increase the number of counts in the particular energy channel from 30 to 42, and setting the threat detection threshold at 103 integral counts. For example, the dwell time could be increased by approximately 40%. Alternatively, the photon beam intensity could be increased without changing the dwell time. In either case, the integral counts expected for minimal quantities would increase from 30 to 42. The desired DP and FP criteria could alternatively be achieved by changing other beam and/or detector parameters to improve either the signal-to-noise ratio or counting statistics. The system may make signal-to-noise measurements and adjust one or beam parameters adaptively, with reference to ROC curves like those of FIG. 4a and FIG. 4b, until the desired DP and FP criteria are achieved.

Individually or together, DP and FP provide a way of describing the efficiency or quality of a particular scan. The detection probability DP and probability of achieving a false positive FP may each be considered a "scan evaluation parameter." The term "detection efficiency criterion" can be used to refer to a particular desired DP value, a particular desired FP value, or a desired combination of a particular DP value and a particular FP value. As is discussed further below, different values or combinations of DP or FP may be desirable for different applications. It will be recognized that other scan evaluation parameters may be used to evaluate the likelihood that an apparent positive signal corresponds to an actual positive (such as the presence in the voxel under scan of a minimum quantity of a certain species).

Where the initial measurement of signal in a particular energy channel of interest exceeds the threat detection threshold with a particular signal-to-noise ratio, the processor 46 can compute one or more scan evaluation parameters and determine whether the detection efficiency criteria are met. If detection efficiency criteria are not met, the precision of the measurement needs to be improved before a positive threat alarm can be sounded with the desired probability of being a true positive. The processor 46 may, for example, alter dwell time, intensity, or other system parameters (such as beam energy, beam collimation, beam filters, detector collimation, detector filters etc.) with reference to such ROC curves in order to achieve dynamically and/or adaptively a desired detection probability (DP) together with a desired limit on the probability of a false positive result (FP). In some embodiments, the system may also adaptively adjust its selection of the desired DP and FP values. For example, the system may conduct a rapid first pass measurement at some value of DP and FP, and then decide based upon the results of that measurement to tighten the criteria and repeat the measurement, adjusting system parameters accordingly. For example, the system can vary the desired DP and FP dependent upon the type of threat detected. This can be useful in allowing some flexibility in weighing the cost of a false positive event against the cost of a failed detection. For example, for threats such as explosives or nuclear weapons, a false positive incurs some costs (such as the unnecessary deployment of police or military specialists), but the cost of a failed detection would be catastrophic. For such threats, the system may be programmed to employ strict detection efficiency criteria of relatively high DP and low FP, resulting in longer or more detailed scans when such threats are initially detected. For threats such as contraband, on the other hand, for which the costs both of failed detection and of false positives may be comparatively lower, the system may be programmed to employ looser detection criteria (comparatively lower DP and higher FP) in the interest of speed and cost-effectiveness of the scanning system.

The system parameters which can be dynamically changed to achieve detection criteria include without limitation:
Photon beam dwell time
Photon beam intensity
Energy of electron beam used in bremsstrahlung source
Spatial resolution of the detector arrays
Angle at which the detector arrays view the target
Spatial resolution and/or geometry of the photon beam
Photon beam filters to reduce contribution of selected isotopes
Photon filters in the photon beam and/or in the detectors
Specific characteristics of the detectors such as integration times, spatial resolution, electronic clustering, etc.

By adjusting one or more of these parameters, the processor 46 can dynamically boost the signal-to-noise ratio or the counting statistics in a particular energy channel of interest. (Those skilled in the art that any system parameter may be adjusted that can affect the signal-to-noise ratio and/or counting statistics.) Thus, for example, as discussed above, if a nominal measurement indicates that a threat detection threshold may have been exceeded, but the statistics or signal-to-noise are not adequate such that the desired maximum rate of false positive threat detection events can be assured, the processor 46 may adjust one or more of the above parameters adaptively during the measurement to determine whether a significant threat detection event has occurred. If, on the other hand, a nominal measurement indicates that no threat detection threshold has been exceeded, the processor 46 may move on to the next voxel for a new nominal measurement without adjusting any beam parameters.

During the measurement of the photons scattered from a particular voxel 50, the processor 46 may continually collect statistics to refine its initial estimate of the background signal, thereby refining the dynamic measurement of signal-to-noise in a particular channel. The processor 46 may thus adjust the estimated detection probability (DP) and probability of obtaining a false positive adaptively in real time, rapidly approaching a measurement of the desired threat detection probability and/or probability of false positives (FP).

If the processor 46 determines that the threat detection threshold in a particular energy channel of interest has been exceeded with a sufficient signal-to-noise ratio to meet a desired detection probability (DP) criterion and that the estimated probability that the event is a false positive is less than some desired FP criterion, it may raise a threat detection alert in any number of ways depending upon the particular threat detected and depending upon the setting in which the system is being employed. For example, in an airport or cargo yard setting, the system may immediately cease the scan and notify an operator that a positive threat detection signal has been detected, at which point the target may be removed and searched. Alternatively, it may mark the particular target (electronically or physically) for quarantine and later search. The action taken by the system upon a positive threat detection signal may vary depending upon the particular threat detected. Other variations of the handling of a positive threat detection signal will be appreciated by those skilled in the art.

The above discussion illustrates that the most efficient non-intrusive scanning algorithm may not necessarily be a uniform scan or a high-resolution scan over the complete volume. This is so for several reasons: First, volumes with very low average density take less time to scan, due to reduced attenuation of the incident beam. Further, low-density regions may not be of interest for inspection of certain threats, such as the presence of high-density shielding (lead) or heavy radioactive materials such as uranium. Moreover, regions of very high Z can be quickly identified by the correspondingly larger attenuation of the incident beam. The search for large quantities of bulk materials can be made at low spatial resolution, such as with an incident photon beam with a wide diameter, or by a fast scan of the beam across the target or of the target through the beam.

In some embodiments, it may be desirable to get much higher spatial resolution on certain regions of interest based on information obtained from other inspection modalities. For example, as illustrated in FIG. 1, a two-dimensional imager such as a conventional x-ray imager 24 may be placed behind the target to detect the intensity of photons transmitted through the target. Alternatively, as illustrated in FIG. 1, transmission NRF detectors 36 may be used with reference scatterers 28 to create a projection image of several nuclear species of interest, identifying regions of relatively high abundance of those species. Where an operator or the processor 46 identifies regions of interest on the resulting two-dimensional projection image (such as dark regions indicating the presence of high-density materials, or regions of high NRF absorption indicating the presence of species of interest), a NRF scan of that region may be performed using the adaptive scanning techniques described above to detect the presence of species of interest in that region.

Figure 5:
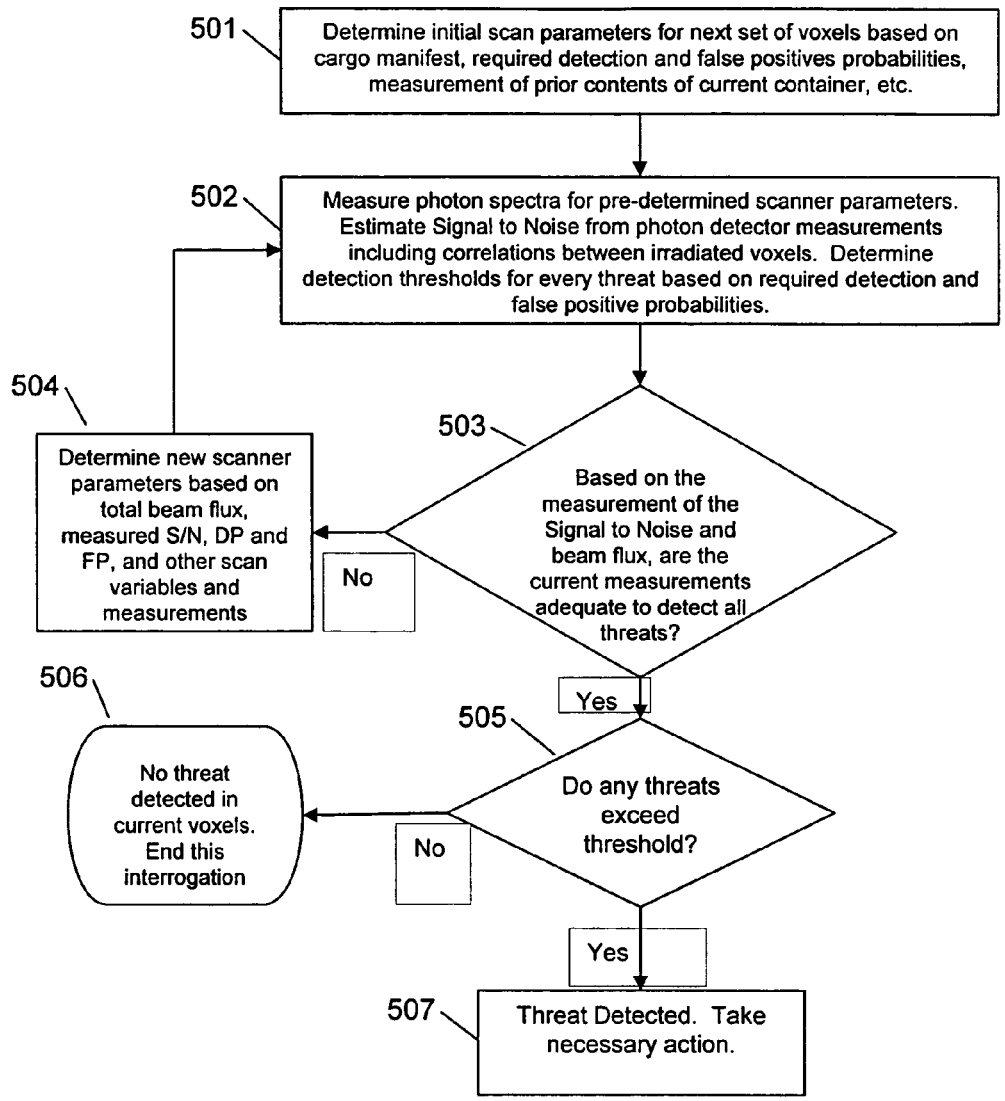
FIG. 5 is a flow chart illustrating an exemplary embodiment of an adaptive scanning method.

An overview of an exemplary embodiment of an adaptive scanning method is illustrated in the flow chart of FIG. 5. In step 501, initial scan parameters are determined for the next voxel or voxels to be scanned. Such initial scan parameters may be computed as described above based upon, for example, one or more of a cargo manifest, a measurement of the average density of the entire container or a portion of it (such as a weight measurement, an NRF density measurement, or a traditional x-ray or CT image). Initial scan parameters determined in step 501 may also take into account the desired detection probability (DP) and probability of obtaining a false positive measurement (FP).

In step 502, scattered or transmitted photon spectra may be measured using the parameters established in step 501. The background spectrum may be estimated as described above, allowing the signal to noise for any detected peaks to be estimated. In one embodiment, the estimated background (and thus the estimated signal to noise) may be improved by searching for correlations in the detected signal in a particular energy channel for adjacent or nearby voxels. (For example, if a relatively large signal is detected in one energy channel for one particular voxel, but no signal is observed above background in the same energy channel for any adjacent voxel, the signal detected in the particular voxel may be correspondingly more likely to be a statistical fluctuation, depending upon the relative size of the voxels and of typical threats associated with the detected isotope.) Detection thresholds for each threat may also be determined using the estimated background signal, taking into account the desired detection probability and probability of obtaining a false positive result. These detection thresholds may be, for example, a number of counts over background in one or more energy channels corresponding to the presence of a threat.

In step 503, the system may decide whether, given the system parameters and the measured signal to noise ratio in each energy channel corresponding to a threat, the current state of the measurement is adequate to detect all threats and/or rule out the presence of all threats within the desired detection probability and probability of obtaining a false positive result. If the system decides that the signal to noise is insufficient to meet those requirements, it proceeds to step 504, in which any of a number of system parameters may be adaptively altered to improve signal to noise and/or counting statistics in one or more energy channels of interest. As described above, such system parameters include beam intensity, electron beam energy, dwell time, the presence or absence of filters in the photon beam or in front of the detectors to reduce signal contributions from known sources, beam or detector collimation, or other parameters. The system may choose the altered system parameters with reference to the desired detection probability (DP) and probability of obtaining a false positive result (FP). (For example, as discussed above, the system may refer to ROC curves computed for various values of signal to noise and numbers of counts in a particular energy channel of interest to determine what increased number of counts would provide the desired detection probability and probability of obtaining a false positive result at the estimated signal-to-noise ratio, and increase the beam intensity accordingly.) After setting new system parameters, the system returns to step 502 to repeat the cycle of measuring the photon spectrum, estimating the background spectrum and signal-to-noise ratio in any energy channel of interest, and determining whether the signal-to-noise ratio is adequate to detect or rule out any threat within the desired detection probability and probability of obtaining a false positive result.

Once the system determines that it has a set of measurements adequate to detect all threats and/or rule out the presence of all threats within the desired detection probability and probability of obtaining a false positive result, it may proceed to step 505. In step 505, the system compares the signal in each energy channel of interest to the threat detection thresholds determined earlier, and decides whether any of the signals exceed those threat detection thresholds. If any threat detection threshold is exceeded, the system may take appropriate action (step 507), such as ceasing the scan and notifying an operator that a positive threat detection signal has been detected or marking the target electronically or physically for quarantine and later search. The system may also be programmed to investigate further upon detection of a positive threat signal. For example, as discussed above, the system may be programmed to make stricter the criteria of desired detection probability and probability of a false positive result in response to a first detection of certain threats. Thus step 507 may include altering the desired detection probability and probability of a false positive result and returning to step 501 to repeat the investigation of the voxel or voxels with the stricter criteria.

If the system determines that there are no signals from the voxel or voxels currently under scan, then it can end the interrogation of that voxel or those voxels, and move on to another voxel or other voxels (step 506).

FIG. 5 and the above discussion illustrate an embodiment of an "inner loop" of an exemplary adaptive scanning and threat detection method. Such an adaptive scanning method may also include an "outer loop" in which the system may select voxels for investigation with the "inner loop" method. For example, as described above, the outer loop may comprise a rapid scanning or imaging step to identify unexpectedly dense or otherwise interesting regions for further scanning. In addition, the outer loop may include searching for correlations in the signals detected in multiple voxels, such as neighboring or nearby voxels. For example, where no individual voxel contains a threshold threat mass of a particular material but several adjacent voxels put together do reach that threshold mass, the system may identify a threat of statistical significance. In another embodiment, the system may use information in neighboring voxels to correct or refine determinations of the attenuation in the photon beam 34 on its approach to a particular voxel, to improve the estimate of the incident flux on the particular voxel so that the determination of the abundance of isotopes in that voxel is properly normalized or so that threshold threat signals are properly set.

The outer loop may also be adaptive; the system may reevalulate the choices of which voxels to interrogate or how to interrogate them based upon the results of scanning other voxels. For example, in one embodiment, where there is a dense (or high atomic number) material in one voxel 50 along the photon beam 34, so that after this voxel 50 the photon beam 34 has been so attenuated that no meaningful measurement can be made of downstream voxels, the system may determine that the target 20 should be rotated (e.g. by 90 or 180 degrees) in order to observe such "hidden" voxels. Alternatively, the system may make an indirect measurement of the density of these hidden voxels by analyzing the attenuation of photons which must pass through the hidden voxels on their way to the detectors when the beam is scanning other voxels elsewhere in the target container 20.

The system may also make threat determinations based upon preprogrammed "knowledge" of threats associated with the presence of certain materials in certain combinations. For example, in a container whose manifest indicates the presence of a large mass of ammonium nitrate fertilizer, a region encompassing many adjacent voxels from which strong nitrogen and oxygen signals are detected may not trigger an inner loop detection event. However, if a significant mass of carbon is also present, the outer loop may detect the possibility of the presence of a diesel ammonium nitrate explosive mixture.

The outer loop may also include adaptively adjusting the detection criteria (detection probability and probability of obtaining a false positive measurement) during the measurement. For example, as discussed above, for some threats the system may be programmed to employ strict detection efficiency criteria (i.e., a relatively high DP value and relatively low FP value), whereas for certain other threats the system may be programmed to employ looser detection criteria (i.e., a comparatively low DP value and comparatively high FP value) in the interest of speed and cost-effectiveness of the scanning system.

While the systems and methods disclosed herein have been particularly shown and described with references to exemplary embodiments thereof, it will be understood by those skilled in the art that various changes in form and details may be made therein without departing from the spirit and scope of the disclosure. Those skilled in the art will recognize or be able to ascertain using no more than routine experimentation, many equivalents to the exemplary embodiments described specifically herein. Such equivalents are intended to be encompassed in the scope of the present disclosure.

What is claimed is:

1. A method for conducting a scan of a target sample for a potential item of interest, the method comprising:
   a) providing a source of photons incident upon the target sample such that some photons are scattered from the target sample;
   b) for at least one portion of interest in the target sample, determining if an incident photon beam intensity into said portion of interest is attenuated as a result of interactions between incident beam photons and portions of the target sample between the said portion of interest and an incident beam source such that the said incident photon beam intensity into the said portion of interest is below a desired flux;
   c) if the incident photon beam intensity into the said portion of interest is below the desired flux, altering an angular orientation between the target sample and the incident photon beam such that the incident photon beam passes through different portions of the target sample than previously in reaching the portion of interest such that the attenuation of the incident photon beam intensity is reduced;
   d) for the said at least one portion of interest in the target sample:
   i) measuring an energy spectrum of photons scattered from the said at least one portion of interest in the target sample;
   ii) using the energy spectrum of photons scattered from the said at least one portion of interest in the target sample to compute a detection probability and a probability of obtaining a false positive result;
   iii) using the measured energy spectrum of photons scattered from the said at least one portion of interest in the target sample to determine whether an item of interest has been detected;
   iv) if an item of interest has not been detected:
   A) determining whether the detection probability meets or exceeds a predetermined desired detection probability;
   B) if the detection probability meets or exceeds the predetermined desired detection probability, ending the scan for the said at least one portion of interest in the target sample; and
   C) if the detection probability does not meet or exceed the predetermined desired detection probability, adjusting one or more system parameters and repeating steps (i) through (iv); and
   v) if an item of interest has been detected:
   A) determining whether the probability that the item of interest detection is a false positive signal exceeds a predetermined desired probability of obtaining a false positive result;
   B) if the probability that the item of interest detection is a false positive signal meets or exceeds the predetermined desired probability of obtaining a false positive result, adjusting one or more system parameters and repeating steps (i) through (v); and
   C) if the probability that the item of interest detection is a false positive signal does not meet or exceed the predetermined desired probability of obtaining a false positive result, identifying a positive item of interest detection event.

2. The method of claim 1, wherein adjusting one or more system parameters comprises at least one of:
   altering an effective dwell time of the photons in a region of the target sample;
   inserting a filter into the source of photons, the filter comprising one or more nuclear species to absorb photons having selected energies or energy regions;
   altering an electron beam energy of an electron beam incident upon a bremsstrahlung target as the photon source;
   altering the intensity of the source of photons;
   altering a collimation of the source of photons;
   altering a collimation of at least one collimated photon detectors;

inserting a filter in front of at least one of the at least one photon detectors, the filter comprising one or more nuclear species to absorb photons having energies falling into selected energy regions;

altering the angle of detection at which at least one of the photon detectors views the target sample relative to the incident photon beam; and altering the spot area in which the incident beam illuminates the target sample at the point of incidence upon the target sample.

3. The method of claim 1, wherein a plurality of photons are transmitted through the sample and the said at least one portion of interest in the target sample is identified by measuring an intensity of at least some of said photons transmitted through the target sample and incident upon a transmission detector.

4. The method of claim 3, wherein adjusting one or more system parameters comprises at least one of:

altering an effective dwell time of the photons in a region of the target sample;

inserting a filter into the source of photons, the filter comprising one or more nuclear species to absorb photons having selected energies or energy regions;

altering an electron beam energy of an electron beam incident upon a bremsstrahlung target as the photon source;

altering the intensity of the source of photons;

altering a collimation of the source of photons;

altering a collimation of at least one collimated photon detectors;

inserting a filter in front of at least one of the at least one photon detectors, the filter comprising one or more nuclear species to absorb photons having energies falling into selected energy regions;

altering the angle of detection at which at least one of the photon detectors views the target sample relative to the incident photon beam; and altering the spot area in which the incident beam illuminates the target sample at the point of incidence upon the target sample.

5. The method of claim 1, wherein a plurality of photons are transmitted through the sample and the said at least one portion of interest in the target sample is identified by measuring an intensity of at least some of said photons transmitted through the target sample and scattered from at least one reference scatterer.

6. The method of claim 5, wherein adjusting one or more system parameters comprises at least one of:

altering an effective dwell time of the photons in a region of the target sample;

inserting a filter into the source of photons, the filter comprising one or more nuclear species to absorb photons having selected energies or energy regions;

altering an electron beam energy of an electron beam incident upon a bremsstrahlung target as the photon source;

altering the intensity of the source of photons;

altering a collimation of the source of photons;

altering a collimation of at least one collimated photon detectors;

inserting a filter in front of at least one of the at least one photon detectors, the filter comprising one or more nuclear species to absorb photons having energies falling into selected energy regions;

altering the angle of detection at which at least one of the photon detectors views the target sample relative to the incident photon beam; and altering the spot area in which the incident beam illuminates the target sample at the point of incidence upon the target sample.

7. A method for detecting in an inspection a potential item of interest in a target sample, the method comprising:

a) providing a source of photons for the inspection;

b) illuminating the target sample with photons from the source during the inspection;

c) providing at least one photon detector to measure an intensity of photons scattered from at least a portion of the target sample in at least one energy channel during the inspection;

d) for at least one portion of interest in the target sample, determining if an incident photon beam intensity into said portion of interest is attenuated as a result of interactions between incident beam photons and portions of the target sample between the said portion of interest and an incident beam source such that the said incident photon beam intensity into the said portion of interest is below a desired flux;

e) if the incident photon beam intensity into the said portion of interest is below the desired flux, altering an angular orientation between the target sample and the incident photon beam such that the incident photon beam passes through different portions of the target sample than previously in reaching the portion of interest such that the attenuation of the incident photon beam intensity is reduced;

f) determining a nominal background signal in at least one energy channel of interest during the inspection;

g) determining whether data collected in at least one of the at least one energy channels of interest during the inspection is sufficient to detect the potential item of interest with a desired statistical precision;

h) if the said data is not sufficient for the said detection, dynamically adjusting one or more system parameters during the inspection based upon at least one measured characteristic of the actual target sample or a portion of the actual target sample to improve a signal-to-noise ratio and/or a statistical precision of data collected in at least one of the at least one energy channels of interest;

i) if the said data is sufficient for the said detection, identifying an item of interest detection event if the intensity of photons detected in at least one of the at least one energy channels of interest during the inspection meets a predetermined item of interest detection criterion.

8. The method of claim 7, wherein adjusting one or more system parameters comprises at least one of:

altering an effective dwell time of the photons in a region of the target sample;

inserting a filter into the source of photons, the filter comprising one or more nuclear species to absorb photons having selected energies or energy regions;

altering an electron beam energy of an electron beam incident upon a bremsstrahlung target as the photon source;

altering the intensity of the source of photons;

altering a collimation of the source of photons;

altering a collimation of at least one collimated photon detectors;

inserting a filter in front of at least one of the at least one photon detectors, the filter comprising one or more nuclear species to absorb photons having energies falling into selected energy regions;

altering the angle of detection at which at least one of the photon detectors views the target sample relative to the incident photon beam; and altering the spot area in which the incident beam illuminates the target sample at the point of incidence upon the target sample.

9. The method of claim 7, wherein a plurality of photons are transmitted through the sample and the said at least one portion of interest is identified by measuring an intensity of photons transmitted through the target sample as a function of a position on the target sample at which the photons illuminate the target sample, using a transmission detector.

10. The method of claim 9, wherein adjusting one or more system parameters comprises at least one of:
   altering an effective dwell time of the photons in a region of the target sample;
   inserting a filter into the source of photons, the filter comprising one or more nuclear species to absorb photons having selected energies or energy regions;
   altering an electron beam energy of an electron beam incident upon a bremsstrahlung target as the photon source;
   altering the intensity of the source of photons;
   altering a collimation of the source of photons;
   altering a collimation of at least one collimated photon detectors;
   inserting a filter in front of at least one of the at least one photon detectors, the filter comprising one or more nuclear species to absorb photons having energies falling into selected energy regions;
   altering the angle of detection at which at least one of the photon detectors views the target sample relative to the incident photon beam; and
   altering the spot area in which the incident beam illuminates the target sample at the point of incidence upon the target sample.

11. The method of claim 7, wherein a plurality of photons are transmitted through the sample and the said at least one portion of interest is identified by measuring an intensity of photons in a specified energy range transmitted through the target sample as a function of a position on the target sample at which the photons illuminate the target sample, using at least one reference scatterer.

12. The method of claim 11, wherein adjusting one or more system parameters comprises at least one of:
   altering an effective dwell time of the photons in a region of the target sample;
   inserting a filter into the source of photons, the filter comprising one or more nuclear species to absorb photons having selected energies or energy regions;
   altering an electron beam energy of an electron beam incident upon a bremsstrahlung target as the photon source;
   altering the intensity of the source of photons;
   altering a collimation of the source of photons;
   altering a collimation of at least one collimated photon detectors;
   inserting a filter in front of at least one of the at least one photon detectors, the filter comprising one or more nuclear species to absorb photons having energies falling into selected energy regions;
   altering the angle of detection at which at least one of the photon detectors views the target sample relative to the incident photon beam; and
   altering the spot area in which the incident beam illuminates the target sample at the point of incidence upon the target sample.

13. A method for conducting a scan of a target sample for a potential item of interest, the method comprising:
   a) providing a source of photons incident upon the target sample such that some photons are scattered from the target sample;
   b) for at least one portion of interest in the target sample:
      i) measuring a time of flight of at least one photon scattered from the target sample and detected in a detector;
      ii) determining by use of the time of flight whether the at least one photon scattered from the target sample was scattered from the at least one portion of interest in the target sample;
      iii) measuring an energy spectrum of photons scattered from the said at least one portion of interest in the target sample;
      iv) using the energy spectrum of photons scattered from the said at least one portion of interest in the target sample to compute a detection probability and a probability of obtaining a false positive result;
      v) using the measured energy spectrum of photons scattered from the said at least one portion of interest in the target sample to determine whether an item of interest has been detected;
      vi) if an item of interest has not been detected:
         A) determining whether the detection probability meets or exceeds a predetermined desired detection probability;
         B) if the detection probability meets or exceeds the predetermined desired detection probability, ending the scan for the said at least one portion of interest in the target sample; and
         C) if the detection probability does not meet or exceed the predetermined desired detection probability, adjusting one or more system parameters and repeating steps (i) through (vi); and
      vii) if an item of interest has been detected:
         A) determining whether the probability that the item of interest detection is a false positive signal exceeds a predetermined desired probability of obtaining a false positive result;
         B) if the probability that the item of interest detection is a false positive signal meets or exceeds the predetermined desired probability of obtaining a false positive result, adjusting one or more system parameters and repeating steps (i) through (vii); and
         C) if the probability that the item of interest detection is a false positive signal does not meet or exceed the predetermined desired probability of obtaining a false positive result, identifying a positive item of interest detection event.

14. The method of claim 13, wherein adjusting one or more system parameters comprises at least one of:
   altering an effective dwell time of the photons in a region of the target sample;
   inserting a filter into the source of photons, the filter comprising one or more nuclear species to absorb photons having selected energies or energy regions;
   altering an electron beam energy of an electron beam incident upon a bremsstrahlung target as the photon source;
   altering the intensity of the source of photons;
   altering a collimation of the source of photons;
   altering a collimation of at least one collimated photon detectors;
   inserting a filter in front of at least one of the at least one photon detectors, the filter comprising one or more nuclear species to absorb photons having energies falling into selected energy regions;
   altering the angle of detection at which at least one of the photon detectors views the target sample relative to the incident photon beam; and
   altering the spot area in which the incident beam illuminates the target sample at the point of incidence upon the target sample.

15. The method of claim 13, wherein a plurality of photons are transmitted through the sample and the said at least one portion of interest in the target sample is identified by measuring an intensity of at least some of said photons transmitted through the target sample.

16. The method of claim 13, wherein some photons are transmitted through the sample and at least a portion of the target sample is identified for further investigation by measuring an intensity of at least some of said photons transmitted through the target sample and scattered from at least one reference scatterer.

17. A method for detecting in an inspection a potential item of interest in a target sample, the method comprising:
    a) providing a source of photons for the inspection;
    b) illuminating the target sample with photons from the source during the inspection;
    c) providing at least one photon detector to measure an intensity of photons scattered from at least one portion of interest in the target sample in at least one energy channel during the inspection;
    d) measuring a time of flight of at least one photon scattered from the target sample and detected in the at least one photon detector;
    e) determining by use of the time of flight whether the at least one photon scattered from the target sample was scattered from the at least one portion of interest in the target sample;
    f) determining a nominal background signal in at least one energy channel of interest during the inspection;
    g) determining whether data collected in at least one of the at least one energy channels of interest during the inspection is sufficient to detect the potential item of interest with a desired statistical precision;
    h) if the said data is not sufficient for the said detection, dynamically adjusting one or more system parameters during the inspection based upon at least one measured characteristic of the actual target sample or a portion of the actual target sample to improve a signal-to-noise ratio and/or a statistical precision of data collected in at least one of the at least one energy channels of interest;
    i) if the said data is sufficient for the said detection, identifying an item of interest detection event if the intensity of photons detected in at least one of the at least one energy channels of interest during the inspection meets a predetermined item of interest detection criterion.

18. The method of claim 17, wherein adjusting one or more system parameters comprises at least one of:
    altering an effective dwell time of the photons in a region of the target sample;
    inserting a filter into the source of photons, the filter comprising one or more nuclear species to absorb photons having selected energies or energy regions;
    altering an electron beam energy of an electron beam incident upon a bremsstrahlung target as the photon source;
    altering the intensity of the source of photons;
    altering a collimation of the source of photons;
    altering a collimation of at least one collimated photon detectors;
    inserting a filter in front of at least one of the at least one photon detectors, the filter comprising one or more nuclear species to absorb photons having energies falling into selected energy regions;
    altering the angle of detection at which at least one of the photon detectors views the target sample relative to the incident photon beam; and
    altering the spot area in which the incident beam illuminates the target sample at the point of incidence upon the target sample.

19. The method of claim 17, wherein a plurality of photons are transmitted through the sample and the said at least one portion of interest is identified by measuring an intensity of photons transmitted through the target sample as a function of a position on the target sample at which the photons illuminate the target sample, using a transmission detector.

20. The method of claim 17, wherein a plurality of photons are transmitted through the sample and the said at least one portion of interest is identified by measuring an intensity of photons in a specified energy range transmitted through the target sample as a function of a position on the target sample at which the photons illuminate the target sample, using at least one reference scatterer.

21. A method for conducting a scan of a target sample for a potential item of interest, the method comprising:
    a) providing a source of photons incident upon the target sample such that some photons are scattered from at least a portion of the target sample and some photons are transmitted through the said at least a portion of the target sample;
    b) measuring an intensity of photons transmitted through the said at least a portion of the target sample;
    c) using a decrease in the measured intensity of photons transmitted through the said at least a portion of the target sample to identify at least one portion of interest in the target sample for further study;
    d) for the said at least one portion of interest in the target sample:
        i) carrying out at least one of the steps of: increasing the dwell time of the photons in the said at least one portion of interest in the target sample; altering the intensity of the source of photons; and altering the spot area in which the incident beam illuminates the at least one portion of interest in the target sample;
        ii) measuring an energy spectrum of photons scattered from the said at least one portion of interest in the target sample; and
        iii) using the measured energy spectrum of photons scattered from the said at least one portion of interest in the target sample to determine whether an item of interest has been detected.

22. The method of claim 21, wherein in response to a determination of at least one of: a probability that the item of interest detection is a false positive signal meets or exceeds a predetermined desired probability of obtaining a false positive result; or an item of interest detection probability does not meet or exceed a predetermined desired item of interest detection probability, at least one system parameter adjustment is made from the group consisting of:
    altering an effective dwell time of the photons in a region of the target sample;
    inserting a filter into the source of photons, the filter comprising one or more nuclear species to absorb photons having selected energies or energy regions;
    altering an electron beam energy of an electron beam incident upon a bremsstrahlung target as the photon source;
    altering the intensity of the source of photons;
    altering a collimation of the source of photons;
    altering a collimation of at least one collimated photon detectors;
    inserting a filter in front of at least one of the at least one photon detectors, the filter comprising one or more nuclear species to absorb photons having energies falling into selected energy regions;

altering the angle of detection at which at least one of the photon detectors views the target sample relative to the incident photon beam; and altering the spot area in which the incident beam illuminates the target sample at the point of incidence upon the target sample.

23. A method for detecting in an inspection a potential item of interest in a target sample, the method comprising:
   a) providing a source of photons for the inspection;
   b) illuminating at least a portion of the target sample with photons from the source during the inspection;
   c) providing at least one photon detector to measure an intensity of photons scattered from at least a portion of the target sample in at least one energy channel during the inspection;
   d) providing a transmission detector for measuring an intensity of photons transmitted through at least a portion of the target sample as a function of a position on the target sample at which the photons illuminate the at least a portion of target sample during the inspection;
   e) using a decrease in the measured intensity of photons transmitted through the said at least a portion of the target sample to identify at least one portion of interest in the target sample for further study;
   f) for the said at least one portion of interest in the target sample, carrying out at least one of the steps of: increasing the dwell time of the photons in the said at least one region of interest in the target sample; altering the intensity of the source of photons; and altering the spot area in which the incident beam illuminates the at least one region of interest in the target sample;
   g) identifying an item of interest detection event if the intensity of photons detected in at least one energy channel of interest during the inspection meets a predetermined item of interest detection criterion.

24. The method of claim 23, wherein in response to a determination that data collected is insufficient to detect a potential item of interest with a desired statistical precision, at least one system parameter adjustment is made from the group consisting of:
   altering adjusting one or more system parameters further comprises at least one of:
   altering an effective dwell time of the photons in a region of the target sample;
   inserting a filter into the source of photons, the filter comprising one or more nuclear species to absorb photons having selected energies or energy regions;
   altering an electron beam energy of an electron beam incident upon a bremsstrahlung target as the photon source;
   altering the intensity of the source of photons;
   altering a collimation of the source of photons;
   altering a collimation of at least one collimated photon detectors;
   inserting a filter in front of at least one of the at least one photon detectors, the filter comprising one or more nuclear species to absorb photons having energies falling into selected energy regions;
   altering the angle of detection at which at least one of the photon detectors views the target sample relative to the incident photon beam; and
   altering the spot area in which the incident beam illuminates the target sample at the point of incidence upon the target sample.

25. A method for conducting a scan of a target sample for a potential item of interest, the method comprising:
   a) providing a source of photons incident upon the target sample such that some photons are scattered from at least a portion of interest of the target sample;
   b) for the said portion of interest of the target sample:
      i) apportioning the portion of the target sample through which an incident photon beam has passed prior to reaching the said portion of interest into at least one voxel, the voxels being configured such that the said incident photon beam successively passes through the voxels in order from a first voxel to a last voxel prior to reaching the said portion of interest;
      ii) measuring photons scattered from the said first voxel;
      iii) based upon the said measurement of photons scattered from the said first voxel, determining an attenuation of the said incident photon beam in passing through the said first voxel, and determining an incident photon beam intensity leaving the said first voxel;
      iv) for each successive voxel, repeating steps ii) and iii) to determine an attenuation of the said incident photon beam in passing through the said voxel, and determining an incident photon beam intensity leaving the said voxel;
      v) measuring an energy spectrum of photons scattered from the said portion of interest of the target sample;
      vi) based upon the said incident photon beam intensity leaving the last voxel before entering the portion of interest of the target sample and the said measured energy spectrum of photons scattered from the said portion of interest of the target sample, determining whether an item of interest has been detected in the portion of interest of the target sample.

26. The method of claim 25, wherein in response to a determination of at least one of: a probability that the item of interest detection is a false positive signal meets or exceeds a predetermined desired probability of obtaining a false positive result, or an item of interest detection probability does not meet or exceed a predetermined desired item of interest detection probability, at least one system parameter adjustment is made from the group consisting of:
   altering an effective dwell time of the photons in a region of the target sample;
   inserting a filter into the source of photons, the filter comprising one or more nuclear species to absorb photons having selected energies or energy regions;
   altering an electron beam energy of an electron beam incident upon a bremsstrahlung target as the photon source;
   altering the intensity of the source of photons;
   altering a collimation of the source of photons;
   altering a collimation of at least one collimated photon detectors;
   inserting a filter in front of at least one of the at least one photon detectors, the filter comprising one or more nuclear species to absorb photons having energies falling into selected energy regions;
   altering the angle of detection at which at least one of the photon detectors views the target sample relative to the incident photon beam; and
   altering the spot area in which the incident beam illuminates the target sample at the point of incidence upon the target sample.

27. A method for detecting in an inspection a potential item of interest in a target sample, the method comprising:
   a) providing a source of photons for the inspection;
   b) illuminating the target sample with photons from the source during the inspection;

c) providing at least one photon detector to measure an intensity of photons scattered from a portion of interest of the target sample in at least one energy channel during the inspection;

e) for the said portion of interest of the target sample:
  i) apportioning the portion of the target sample through which an incident photon beam has passed prior to reaching the said portion of interest into at least one voxel, the voxels being configured such that the said incident photon beam successively passes through the voxels in order from a first voxel to a last voxel prior to reaching the said portion of interest;
  ii) measuring photons scattered from the said first voxel;
  iii) based upon the said measurement of photons scattered from the said first voxel, determining an attenuation of the said incident photon beam in passing through the said first voxel, and determining an incident photon beam intensity leaving the said first voxel;
  iv) for each successive voxel, repeating steps ii) and iii) to determine an attenuation of the said incident photon beam in passing through the said voxel, and determining an incident photon beam intensity leaving the said voxel;
  v) measuring an energy spectrum of photons scattered from the said portion of interest of the target sample;
  vi) based upon the said incident photon beam intensity leaving the last voxel before entering the portion of interest of the target sample and the said measured energy spectrum of photons scattered from the said portion of interest of the target sample, determining whether an item of interest has been detected in the portion of interest of the target sample.

28. The method of claim 27, wherein in response to a determination that data collected is insufficient to detect a potential item of interest with a desired statistical precision, at least one system parameter adjustment is made from the group consisting of:
  altering an effective dwell time of the photons in a region of the target sample;
  inserting a filter into the source of photons, the filter comprising one or more nuclear species to absorb photons having selected energies or energy regions;
  altering an electron beam energy of an electron beam incident upon a bremsstrahlung target as the photon source;
  altering the intensity of the source of photons;
  altering a collimation of the source of photons;
  altering a collimation of at least one collimated photon detectors;
  inserting a filter in front of at least one of the at least one photon detectors, the filter comprising one or more nuclear species to absorb photons having energies falling into selected energy regions;
  altering the angle of detection at which at least one of the photon detectors views the target sample relative to the incident photon beam; and
  altering the spot area in which the incident beam illuminates the target sample at the point of incidence upon the target sample.

29. A method for creating a three-dimensional image of a distribution of an item of interest in a target sample of interest, the method comprising:
  a) apportioning the target sample into voxels;
  b) providing a source of photons incident upon the target sample such that some photons are scattered from at least a portion of the sample;
  c) for each voxel of interest:
    i) measuring an energy spectrum of photons scattered from the said voxel of interest;
    ii) in response to a determination of at least one of: a probability that the item of interest detection for the said voxel of interest is a false positive signal meets or exceeds a predetermined desired probability of obtaining a false positive result, or an item of interest detection probability for the said voxel of interest does not meet or exceed a predetermined desired item of interest detection probability, making at least one system parameter adjustment from the group consisting of:
      altering an effective dwell time of the photons in a region of the target sample;
      inserting a filter into the source of photons, the filter comprising one or more nuclear species to absorb photons having selected energies or energy regions;
      altering an electron beam energy of an electron beam incident upon a bremsstrahlung target as the photon source;
      altering the intensity of the source of photons;
      altering a collimation of the source of photons;
      altering a collimation of at least one collimated photon detectors;
      inserting a filter in front of at least one of the at least one photon detectors, the filter comprising one or more nuclear species to absorb photons having energies falling into selected energy regions;
      altering the angle of detection at which at least one of the photon detectors views the target sample relative to the incident photon beam; and
      altering the spot area in which the incident beam illuminates the target sample at the point of incidence upon the target sample;
    iii) using the measured energy spectrum of photons scattered from the said voxel of interest to determine whether an item of interest has been detected in the voxel of interest; and
  d) creating the three-dimensional image of the distribution of the item of interest in the target sample using the determinations of whether the item of interest has been detected in each voxel of interest.

30. A method for creating a three-dimensional image of a distribution of an item of interest in a target sample of interest, the method comprising:
  a) apportioning the target sample into voxels;
  b) providing a source of photons for the inspection;
  c) illuminating the target sample with photons from the source during the inspection;
  d) providing at least one photon detector to measure an intensity of photons scattered from at least a portion of the target sample in at least one energy channel during the inspection;
  e) for each voxel of interest, measuring the energy spectrum of photons scattered from the said voxel of interest;
  f) in response to a determination that data collected for the said voxel of interest is insufficient to detect a potential item of interest in the said voxel of interest with a desired statistical precision, making at least one system parameter adjustment from the group consisting of:
    altering an effective dwell time of the photons in a region of the target sample;
    inserting a filter into the source of photons, the filter comprising one or more nuclear species to absorb photons having selected energies or energy regions;
    altering an electron beam energy of an electron beam incident upon a bremsstrahlung target as the photon source;
    altering the intensity of the source of photons;
    altering a collimation of the source of photons;
    altering a collimation of at least one collimated photon detectors;

inserting a filter in front of at least one of the at least one photon detectors, the filter comprising one or more nuclear species to absorb photons having energies falling into selected energy regions;

altering the angle of detection at which at least one of the photon detectors views the target sample relative to the incident photon beam; and altering the spot area in which the incident beam illuminates the target sample at the point of incidence upon the target sample.

g) for each voxel of interest, using the measured energy spectrum of photons scattered from the said voxel of interest to determine whether an item of interest has been detected in the voxel of interest of the target sample; and h) creating the three-dimensional image of the distribution of the item of interest in the target sample using the determinations of whether the item of interest has been detected in each voxel of interest.

31. A method for conducting a scan of a target sample for a potential item of interest, the method comprising:

a) providing a source of photons incident upon the target sample such that some photons are scattered from the sample and some photons are transmitted through the sample;

b) providing at least one reference scatterer, each of which at least one reference scatterer comprises at least one nuclear species of interest;

c) for each of the at least one reference scatterer, using the measured intensity of photons transmitted through at least one portion of the target sample and scattered from the said reference scatterer to determine a quantity of the at least one nuclear species of interest in the at least one portion of the target sample;

d) using the quantity of the at least one nuclear species of interest in the at least one portion of the target sample, determining at least one portion of interest in the target sample;

e) for at least one of the at least one portions of interest:

i) measuring an energy spectrum of photons scattered from the portion of interest;

ii) using the energy spectrum of photons scattered from the portion of interest to compute a detection probability and a probability of obtaining a false positive result;

iii) using the measured energy spectrum of photons scattered from the portion of interest to determine whether an item of interest has been detected;

iv) if an item of interest has not been detected:

A) determining whether the detection probability meets or exceeds a predetermined desired detection probability;

B) if the detection probability meets or exceeds the predetermined desired detection probability, ending the scan for the portion of interest; and C) if the detection probability does not meet or exceed the predetermined desired detection probability, adjusting one or more system parameters and repeating steps (i) through (iv); and v) if an item of interest has been detected:

A) determining whether the probability that the item of interest detection is a false positive signal exceeds a predetermined desired probability of obtaining a false positive result;

B) if the probability that the item of interest detection is a false positive signal meets or exceeds the predetermined desired probability of obtaining a false positive result, adjusting one or more system parameters and repeating steps (i) through (v); and C) if the probability that the item of interest detection is a false positive signal does not meet or exceed the predetermined desired probability of obtaining a false positive result, identifying a positive item of interest detection event.

32. The method of claim 31, wherein there are at least two reference scatterers, each comprising a different nuclear species of interest.

33. The method of claim 31, wherein in response to a determination of at least one of: the probability that the item of interest detection is a false positive signal meets or exceeds the predetermined desired probability of obtaining a false positive result, or the detection probability does not meet or exceed the predetermined desired detection probability, at least one system parameter adjustment is made from the group consisting of:

altering an effective dwell time of the photons in a region of the target sample;

inserting a filter into the source of photons, the filter comprising one or more nuclear species to absorb photons having selected energies or energy regions;

altering an electron beam energy of an electron beam incident upon a bremsstrahlung target as the photon source;

altering the intensity of the source of photons;

altering a collimation of the source of photons;

altering a collimation of at least one collimated photon detectors;

inserting a filter in front of at least one of the at least one photon detectors, the filter comprising one or more nuclear species to absorb photons having energies falling into selected energy regions;

altering the angle of detection at which at least one of the photon detectors views the target sample relative to the incident photon beam; and altering the spot area in which the incident beam illuminates the target sample at the point of incidence upon the target sample.

34. A method for detecting in an inspection a potential item of interest in a target sample, the method comprising:

a) providing a source of photons for the inspection;

b) illuminating the target sample with photons from the source during the inspection;

c) providing at least one reference scatterer during the inspection, each of which at least one reference scatterer comprising at least one nuclear species of interest;

d) allowing photons transmitted through the target sample to scatter from the at least one reference scatterer during the inspection;

e) providing at least one reference-photon detector to measure an intensity of photons scattered from the at least one reference scatterer in at least one reference-photon energy channel of interest as a function of a position on the target sample at which the photons illuminate the target sample during the inspection;

f) for each of the at least one reference scatterers, using the intensity of photons measured by at least one of the at least one reference-photon detectors in at least one of the at least one reference-photon energy channels of interest to determine a quantity of the at least one nuclear species of interest in at least one portion of the target sample;

g) using the quantity of the at least one nuclear species of interest in the at least one portion of the target sample, determining at least one portion of interest for further scanning during the inspection;

h) providing at least one scattered-photon detector to measure an intensity of photons scattered from at least one of the at least one portion of interest in the target sample in at least one scattered-photon energy channel during the inspection;
i) determining a nominal background signal in at least one scattered-photon energy channel of interest during the inspection;
j) determining whether data collected in at least one of the at least one scattered-photon energy channels of interest during the inspection is sufficient to detect the potential item of interest with a desired statistical precision;
k) if the said data is not sufficient for the said detection, dynamically adjusting one or more system parameters during the inspection based upon at least one measured characteristic of the actual target sample or a portion of the actual target sample to improve a signal-to-noise ratio and/or a statistical precision of data collected in at least one of the at least one scattered-photon energy channels of interest;
l) if the said data is sufficient for the said detection, identifying an item of interest detection event if the intensity of photons detected in at least one of the at least one scattered-photon energy channels of interest during the inspection meets a predetermined item of interest detection criterion.

35. The method of claim 34, wherein there are at least two reference scatterers, each comprising a different nuclear species of interest.

36. The method of claim 34, wherein in response to a determination that data collected is insufficient to detect a potential item of interest with a desired statistical precision, at least one system parameter adjustment is made from the group consisting of:
  altering an effective dwell time of the photons in a region of the target sample;
  inserting a filter into the source of photons, the filter comprising one or more nuclear species to absorb photons having selected energies or energy regions;
  altering an electron beam energy of an electron beam incident upon a bremsstrahlung target as the photon source;
  altering the intensity of the source of photons;
  altering a collimation of the source of photons;
  altering a collimation of at least one collimated photon detectors;
  inserting a filter in front of at least one of the at least one photon detectors, the filter comprising one or more nuclear species to absorb photons having energies falling into selected energy regions;
  altering the angle of detection at which at least one of the photon detectors views the target sample relative to the incident photon beam; and
  altering the spot area in which the incident beam illuminates the target sample at the point of incidence upon the target sample.

37. A method for conducting a scan of a target sample for a potential nuclear species of interest, the method comprising:
  a) providing a source of photons incident upon the target sample such that some photons are transmitted through at least a portion of the sample;
  b) providing a reference scatterer, comprising at least one nuclear species of interest;
  c) providing a second complimentary reference scatterer comprising at least one different nuclear species, such that in the said at least one different nuclear species a nuclear resonance occurs at a photon frequency close to that at which a nuclear resonance occurs in the nuclear species of interest in the reference scatterer to which the second reference scatterer is complimentary;
  d) using the measured intensity of photons transmitted through at least one portion of the target sample and scattered from the said second complimentary reference scatterer to determine an attenuation for the photon beam crossing the at least one portion of the target sample;
  e) in response to a determination of at least one of: the probability that the determination of the presence of the nuclear species of interest in a quantity above a predetermined threshold in the said portion of the target sample is a false positive signal meets or exceeds the predetermined desired probability of obtaining a false positive result, or the detection probability for detecting the presence of the nuclear species of interest in a quantity above a predetermined threshold in the said portion of the target sample does not meet or exceed the predetermined desired detection probability, making at least one system parameter adjustment from the group consisting of:
  altering an effective dwell time of the photons in a region of the target sample;
  inserting a filter into the source of photons, the filter comprising one or more nuclear species to absorb photons having selected energies or energy regions;
  altering an electron beam energy of an electron beam incident upon a bremsstrahlung target as the photon source;
  altering the intensity of the source of photons;
  altering a collimation of the source of photons;
  altering a collimation of at least one collimated photon detectors;
  inserting a filter in front of at least one of the at least one photon detectors, the filter comprising one or more nuclear species to absorb photons having energies falling into selected energy regions;
  altering the angle of detection at which at least one of the photon detectors views the target sample relative to the incident photon beam; and
  altering the spot area in which the incident beam illuminates the target sample at the point of incidence upon the target sample; and
  f) using the attenuation for the photon beam crossing the at least one portion of the target sample, and the measured intensity of photons transmitted through the said at least one portion of the target sample and scattered from the said reference scatterer to determine if the quantity of the nuclear species of interest in the at least one portion of the target sample is above the predetermined threshold.

38. A method for detecting in an inspection a nuclear species of interest in a target sample, the method comprising:
  a) providing a source of photons for the inspection;
  b) illuminating the target sample with photons from the source during the inspection;
  c) providing a reference scatterer during the inspection, comprising at least one nuclear species of interest;
  d) providing a second complimentary reference scatterer comprising at least one different nuclear species, such that in the said at least one different nuclear species a nuclear resonance occurs at a photon frequency close to that at which a nuclear resonance occurs in the nuclear species of interest in the reference scatterer to which the second reference scatterer is complimentary;
  e) allowing photons transmitted through the target sample to scatter from the reference scatterer and the second complimentary reference scatterer during the inspection;

f) providing at least one reference-photon detector to measure an intensity of photons scattered from the reference scatterer and the second complimentary reference scatterer in at least one reference-photon energy channel of interest as a function of a position on the target sample at which the photons illuminate the target sample during the inspection;

g) using the measured intensity of photons transmitted through at least one portion of the target sample and scattered from the said second complimentary reference scatterer to determine an attenuation for the photon beam crossing the at least one portion of the target sample;

h) in response to a determination that data collected is insufficient to determine the presence of the nuclear species of interest in a quantity above a predetermined threshold with a desired statistical precision in the said portion of the target sample, making at least one system parameter adjustment from the group consisting of:

altering an effective dwell time of the photons in a region of the target sample;

inserting a filter into the source of photons, the filter comprising one or more nuclear species to absorb photons having selected energies or energy regions;

altering an electron beam energy of an electron beam incident upon a bremsstrahlung target as the photon source;

altering the intensity of the source of photons;

altering a collimation of the source of photons;

altering a collimation of at least one collimated photon detectors;

inserting a filter in front of at least one of the at least one photon detectors, the filter comprising one or more nuclear species to absorb photons having energies falling into selected energy regions;

altering the angle of detection at which at least one of the photon detectors views the target sample relative to the incident photon beam; and altering the spot area in which the incident beam illuminates the target sample at the point of incidence upon the target sample.

i) using the attenuation for the photon beam crossing the at least one portion of target sample, and the measured intensity of photons transmitted through the said at least one portion of the target sample and scattered from the said reference scatterer to determine if the quantity of the nuclear species of interest in the at least one portion of the target sample is above the predetermined threshold.

39. A method for creating a two-dimensional image of a distribution of a nuclear species of interest in a target sample, the method comprising:

a) providing a reference scatterer, comprising at least one nuclear species of interest;

b) providing a second complimentary reference scatterer comprising at least one different nuclear species, such that in the said at least one different nuclear species a nuclear resonance occurs at a photon frequency close to that at which a nuclear resonance occurs in the nuclear species of interest in the reference scatterer to which the second reference scatterer is complimentary;

c) providing a source of photons incident upon the target sample such that some photons are transmitted through at least a portion of the sample;

d) using the measured intensity of photons transmitted through the said portion of the target sample and scattered from the said second complimentary reference scatterer to determine an attenuation for the photon beam crossing the said portion of the target sample;

e) in response to a determination of at least one of: the probability that the determination of the presence of the nuclear species of interest in a quantity above a predetermined threshold in the said portion of the target sample is a false positive signal meets or exceeds the predetermined desired probability of obtaining a false positive result, or the detection probability for detecting the presence of the nuclear species of interest in a quantity above a predetermined threshold in the said portion of the target sample does not meet or exceed the predetermined desired detection probability, making at least one system parameter adjustment from the group consisting of:

altering an effective dwell time of the photons in a region of the target sample;

inserting a filter into the source of photons, the filter comprising one or more nuclear species to absorb photons having selected energies or energy regions;

altering an electron beam energy of an electron beam incident upon a bremsstrahlung target as the photon source;

altering the intensity of the source of photons;

altering a collimation of the source of photons;

altering a collimation of at least one collimated photon detectors;

inserting a filter in front of at least one of the at least one photon detectors, the filter comprising one or more nuclear species to absorb photons having energies falling into selected energy regions;

altering the angle of detection at which at least one of the photon detectors views the target sample relative to the incident photon beam; and altering the spot area in which the incident beam illuminates the target sample at the point of incidence upon the target sample; and f) using the attenuation for the photon beam crossing the said portion of the target sample, and the measured intensity of photons transmitted through the said portion of the target sample and scattered from the said reference scatterer to determine if the quantity of the nuclear species of interest in the said portion of the target sample is above the predetermined threshold;

g) repeating steps c)-f) with respect to at least one other portion of the target sample; and h) creating the two-dimensional image of the distribution of the nuclear species of interest in the target sample.

40. A method for creating a two-dimensional image of a distribution of a nuclear species of interest in a target sample, the method comprising:

a) providing a source of photons for the inspection;

b) illuminating the target sample with photons from the source during the inspection;

c) providing a reference scatterer during the inspection, comprising at least one nuclear species of interest;

d) providing a second complimentary reference scatterer comprising at least one different nuclear species, such that in the said at least one different nuclear species a nuclear resonance occurs at a photon frequency close to that at which a nuclear resonance occurs in the nuclear species of interest in the reference scatterer to which the second reference scatterer is complimentary;

e) allowing photons transmitted through the target sample to scatter from the reference scatterer and the second complimentary reference scatterer during the inspection;

f) providing at least one reference-photon detector to measure an intensity of photons scattered from the reference scatterer and the second complimentary reference scatterer in at least one reference-photon energy channel of interest as a function of a position on the target sample at which the photons illuminate the target sample during the inspection;

g) using the measured intensity of photons transmitted through a portion of the target sample and scattered from the said second complimentary reference scatterer to determine an attenuation for the photon beam crossing the said portion of the target sample;

h) in response to a determination that data collected is insufficient to determine the presence of the nuclear species of interest in a quantity above a predetermined threshold with a desired statistical precision in the said portion of the target sample, making at least one system parameter adjustment from the group consisting of:

altering an effective dwell time of the photons in a region of the target sample;

inserting a filter into the source of photons, the filter comprising one or more nuclear species to absorb photons having selected energies or energy regions;

altering an electron beam energy of an electron beam incident upon a bremsstrahlung target as the photon source;

altering the intensity of the source of photons;

altering a collimation of the source of photons;

altering a collimation of at least one collimated photon detectors;

inserting a filter in front of at least one of the at least one photon detectors, the filter comprising one or more nuclear species to absorb photons having energies falling into selected energy regions;

altering the angle of detection at which at least one of the photon detectors views the target sample relative to the incident photon beam; and altering the spot area in which the incident beam illuminates the target sample at the point of incidence upon the target sample.

i) using the attenuation for the photon beam crossing the said portion of the target sample, and the measured intensity of photons transmitted through the said portion of the target sample and scattered from the said reference scatterer to determine if the quantity of the nuclear species of interest in the said portion of the target sample is above the predetermined threshold;

j) repeating steps g)-i) with respect to at least one other portion of the target sample; and k) creating the two-dimensional image of the distribution of the nuclear species of interest in the target sample.

* * * * *